(12) United States Patent
Houge et al.

(10) Patent No.: US 7,342,225 B2
(45) Date of Patent: Mar. 11, 2008

(54) CRYSTALLOGRAPHIC METROLOGY AND PROCESS CONTROL

(75) Inventors: Erik C. Houge, Orlando, FL (US); Brian Kempshall, Casselberry, FL (US); Stephen M. Schwarz, Merritt Island, FL (US); Fred A. Stevie, Cary, NC (US)

(73) Assignee: Agere Systems, Inc., Allentown, PA (US)

( * ) Notice: Subject to any disclaimer, the term of this patent is extended or adjusted under 35 U.S.C. 154(b) by 365 days.

(21) Appl. No.: 10/505,198

(22) PCT Filed: Feb. 24, 2003

(86) PCT No.: PCT/US03/07264

§ 371 (c)(1), (2), (4) Date: Mar. 2, 2005

(87) PCT Pub. No.: WO03/073481

PCT Pub. Date: Sep. 4, 2003

(65) Prior Publication Data

US 2006/0231752 A1  Oct. 19, 2006

Related U.S. Application Data

(60) Provisional application No. 60/359,222, filed on Feb. 22, 2002.

(51) Int. Cl.
*H01J 37/28* (2006.01)
*H01J 37/256* (2006.01)
*G01N 23/00* (2006.01)

(52) U.S. Cl. .............. 250/306; 250/307; 250/310; 117/902

(58) Field of Classification Search .............. None
See application file for complete search history.

(56) References Cited

U.S. PATENT DOCUMENTS

| 5,463,977 A | 11/1995 | Manada et al. |
| 6,577,970 B2* | 6/2003 | Houge et al. .............. 702/81 |
| 2006/0048697 A1* | 3/2006 | Houge et al. .............. 117/11 |

* cited by examiner

*Primary Examiner*—Nikita Wells

(57) ABSTRACT

A system (70) for crystallography including a sample holder (74), an electron source (76) for generating an electron beam, and a scanning actuator (80) for controlling the relative movement between the electron beam and the crystalline sample, the scanning actuator being controllable for directing the electron beam at a series of spaced apart points within the sample area. The system also includes an image processor (84) for generating crystallographic data based upon electron diffraction from the crystalline sample and for determining whether sufficient data have been acquired to characterize the sample area. The system further includes a controller (86) for controlling the scanning actuator to space the points apart such that acquired data is representative of a different grains within the crystalline sample. IN other embodiments, the invention includes one or more ion beams (178, 188) for crystallography and a combination ion beam/electron beam (218, 228).

52 Claims, 37 Drawing Sheets

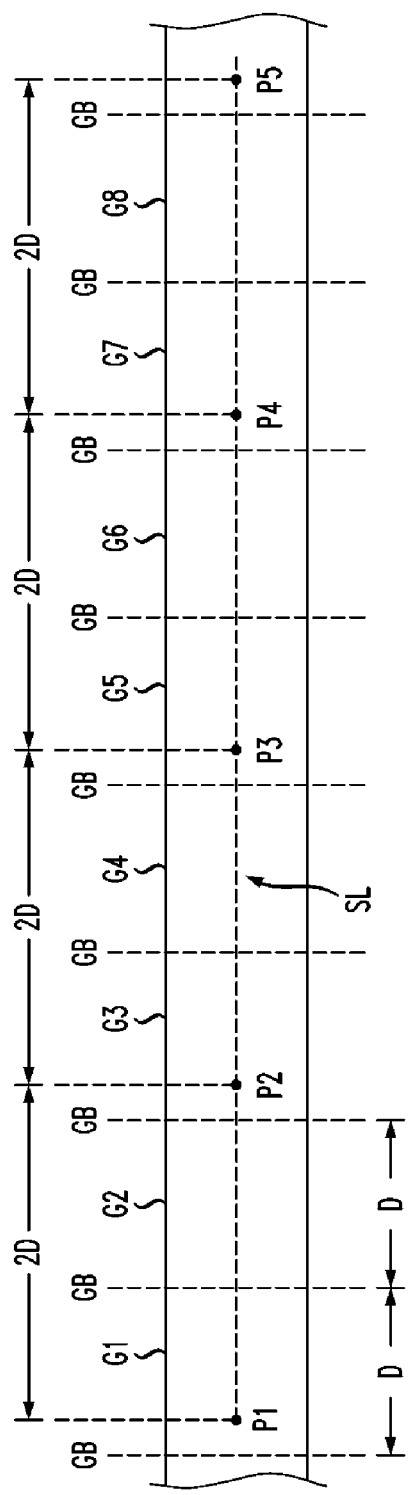

7.00 μm = 35 steps 4.50 μm = 45 steps   IPF Map [001]

200

250

252

BIOCRYSTAL MOLD SCHEMATIC

FIG. 33A

| h k l | x y z | Tol | Frac |
|---|---|---|---|
| 0 0 -1 | 0 0 1 | 10.00 | 0.00 |
| 1 -1 0 | 0 0 1 | 10.00 | 0.97 |
| 1 -1 -1 | 0 0 1 | 10.00 | 0.00 |
| 0 -1 5 | 0 0 1 | 10.00 | 0.00 |
| 1 1 4 | 0 0 1 | 10.00 | 0.02 |

FIG. 33B

| h k l | x y z | Tol | Frac |
|---|---|---|---|
| 0 0 -1 | 0 0 1 | 10.00 | 0.00 |
| 1 -1 0 | 0 0 1 | 10.00 | 0.84 |
| 1 -1 -1 | 0 0 1 | 10.00 | 0.00 |
| 0 -1 5 | 0 0 1 | 10.00 | 0.04 |
| 1 1 4 | 0 0 1 | 10.00 | 0.14 |

CRYSTALLOGRAPHIC METROLOGY AND PROCESS CONTROL

This application claims the benefit of the Feb. 22, 2002, filing date of U.S. provisional patent application No. 60/359,222 incorporated herein by reference.

FIELD OF THE INVENTION

The present invention relates to crystallography, and, more particularly, to crystallographic system and methods for inline metrology and process control.

BACKGROUND OF THE INVENTION

Some of the primary concerns in the manufacture of semiconductor devices are the mechanical and electrical properties of the metallization used to carry electrons within the semiconductor device. As the manufacturing technology of semiconductors becomes more sophisticated, the physical properties of the materials used in semiconductor device, such as the complexity of preferred orientations of polycrystalline microstructures, becomes increasingly important. Crystallographic orientation, grain size and grain morphology play major roles in the reliability, quality assurance, electrical migration resistance, electrical properties, chemical-mechanical polishing (CMP) removal rates, and CMP endpoint detectability. In particular, crystallography plays a role in many aspects of a CMP process, such as the determination of CMP rate curves, the polishing time, the pressure on the wafer and pad, the speed of rotation and the slurry feed rate and chemistry, such as polarity. U.S. patent application Ser. No. 10/121,370, incorporated herein by reference, describes adjusting solvent polarities in a CMP slurry to compensate for differential removal rates.

One of the problems with current manufacturing systems is that process steps within a semiconductor line are treated as discrete steps, which are considered to be independent of the step preceding or following them. CMP is one such step. It is not generally known in the art that chemical mechanical planarization is heavily dependent on the morphological and crystallographic nature of the metal put down during the deposition process.

The crystallographic microstructure can be examined with a variety of techniques. Multiphase two-dimensional mapping of crystallographic and morphological data provides challenges to determine the crystallographic grain orientation, grain size and grain boundaries of a crystalline sample. There are numerous ways of obtaining this information, but each of the methods presents slightly different information that the others do not.

The processing of materials in the semiconductor industry to achieve smaller geometries introduces new problems as the boundaries between grain structures and the orientations of the boundaries become more critical. For example, the conventional method of indexing Kikuchi diffraction patterns over a scanned area is one method of determining both the crystallographic orientation and grain morphology of thin films on sample surfaces. Backscattering Kikuchi Diffraction (BKD) in a scanning electron microscope (SEM) can produce Kikuchi bands from polycrystalline grains approaching the size of the probe diameter. By applying the rules of point group symmetry to the Kikuchi bands, characteristics such as crystallographic grain orientation and grain size within a specimen can be determined.

Grains within polycrystalline materials generally have orientations that vary from grain to grain. This variation, when considered over a bulk specimen area, can lead to the directional grouping of specific crystalline planes with respect to certain crystallographic axes. The "preferred orientation" of a polycrystalline sample refers to an average, or overall, orientation of the grains. Multiple preferred orientations can also exist simultaneously within a sample. The complexity of the preferred orientation of polycrystalline microstructures can be examined with a technique known as Orientation Imaging Microscopy, which analyzes collections of BKD patterns. This technique combines the advantages of point orientation in Transmission Electron Microscopy (TEM) with morphological information over a large enough area to provide statistical relevance.

For example, aluminum deposited by chemical vapor deposition (CVD) deposits in a preferred orientation along a (111) fiber texture normal to a silicon substrate. This geometry is preferred to reduce electromigration. BKD pattern analysis can be used to quantify the quality of the deposition of the aluminum along the preferential crystallographic axis.

The movement of the semiconductor industry to copper metallization will require seed layers and barrier layers made out of tantalum nitride, for example. The deposition of copper by CVD does not seem to exhibit preferential orientation. This results in a variable that can differ between deposited copper films. BKD analysis provides a way of quantifying the films for orientation analysis in a two-dimensional mapping array whereby the preferred grain orientations can be compared from one film to another.

BKD pattern analysis works by collecting a Kikuchi pattern at a specific location on a sample surface, converting the pattern to a Hough space where each line is represented as a spot, and using the angular deviations between the spots to calculate the crystallographic orientation of the crystal at that location. The scanning electron microscope beam or the sample stage is then stepped to the next point and the process is repeated. The stepping occurs in a raster pattern with a fixed step size over the entire scan area. Unfortunately, this method is very time consuming. For example, to acquire a pattern from an area that is 10 square micrometers with a step size of 50 nm, approximately 40,000 individual Kikuchi patterns must be collected and analyzed. With each Kikuchi pattern typically taking approximately 0.5 seconds, this yields a scan time for the entire area of approximately 11 hours.

The pattern also has a maximum grain boundary resolution of 50 nm. The lengthy collection time of these patterns makes automated BKD pattern analysis labor intensive and time consuming. Increasing the step size does decrease the time element involved in obtaining and analyzing date with respect to certain characteristics of a polycrystalline material.

Ion channeling is another technique used, for example, to study defect concentrations in crystals. When an ion beam is aligned along a major crystal axis or plane, ion-atom interaction probability is significantly reduced, resulting in a large reduction of scattering events and deeper penetration of ions into the crystal structure. Accordingly, a secondary electron signal can be detected and analyzed to determine channel locations, and thus some basic morphology of the crystal, for example, by comparison to a reference crystal. Angle resolved channeling (ARC) of crystal planes about different axes can be obtained by adjusting the sample orientation in incremental angular steps. Data is acquired at each angle and an accumulated data set of backscattered spectra at each angle is used to create an image of the crystal structure. The main difficulty with resolving discrete crystallographic information from ion channeling is due to the overlap in contrast intensities for different crystalline orientations.

The foregoing metrological techniques are conducted off-line, i.e., by taking partially fabricated structures in fabrication, including semiconductor devices, out of the manufacturing sequence. However, inline metrology techniques that identify either grain size or preferred orientation of polycrystalline films do not exist. Semiconductor devices are typically destructively measured offline by time consuming techniques of electron diffraction and x-ray diffraction. The disadvantage of these offline techniques is that they are destructive and require constant monitoring on test structures and wafers, which results in a window between when problems occur and when problems are detected.

Current micro-electronics manufacturing methods incorporate metrology methods, such as the methods described above, for the purpose of downstream quality control. For example, once a photoresist process has been completed, it is known to utilize a scanning electron microscope or other metrology technique to measure how closely the photoresist mask corresponds to its intended configuration. A go/no-go parameter may be established, and semiconductor wafers having photoresist patterns that are outside of the acceptance limits are removed from the production line for subsequent rework. Wafers having acceptable photoresist masks are then processed through a further manufacturing step, such as for example, an etching process. A second metrology step may then be used to confirm that the resulting hard mask product falls within predetermined acceptance limits.

In spite of the numerous advances in micro-electronics manufacturing techniques, there remain many aspects of various processes that are not fully understood by those skilled in the art. The control of many micro-electronics manufacturing techniques includes a significant amount of uncertainty. Plasma etch processes are generally difficult to control, with variations occurring from wafer to wafer and from lot to lot. Uncertainties may be induced by machine aging and cleaning lead times, run-to-run variations in wafer attributes, and chemistry of the plasma. Quality control is essentially a feed-back process, i.e. the output product is measured to determine if it is acceptable, and if it is unacceptable, a control parameter is changed. The output product is then again measured to see if the desired corrective effect has been achieved. This cycle is repeated until an acceptable output product is achieved. Each step in the manufacturing process is controlled in a similar manner. For example, to achieve a desired etch pattern, there must first be a photoresist development step then an etching step. Current quality control processes involve a first metrology step on the developed photoresist pattern, then a second metrology step on the etched wafer surface. Each of these steps are treated separately, and each has its own range of acceptable variation from the ideal design value. Because these processes are both complicated and not fully understood, there has been no effort in the industry to integrate the quality control aspects of the overall manufacturing process. Such a control scheme is naturally rigid, allows for the build-up of unfavorable tolerances, and provides no capacity for accommodating deficiencies in one process with counterbalancing variations in another process.

It is known to apply a neural network to the control of a semiconductor wafer etching process. Both U.S. Pat. No. 5,653,894 issued to Ibbotson, et al., and U.S. Pat. No. 5,737,496 issued to Frye, et al, describe the use of neural networks to control the endpoint in a plasma etch process. While such systems provide a degree of in-process control for an etch process, further improvements are desired.

SUMMARY OF THE INVENTION

A system for crystallography and process control is described herein as including: a sample holder for holding a crystalline sample for characterization of a sample area; an electron source for generating an electron beam; a scanning actuator for controlling the relative movement between the electron beam and the crystalline sample, the scanning actuator being controllable for directing the electron beam at a series of spaced apart points within the sample area The system also includes: a first processing system for generating crystallographic data based upon electron diffraction from the crystalline sample; a second processing system configured for determining whether sufficient data have been acquired to characterize the sample area; and a controller for controlling the scanning actuator to space the points apart such that acquired data is representative of a different grains within the crystalline sample. The system may also include a first ion source for generating a first ion beam; an electron detector for detecting secondary electrons emitted from the crystalline sample; and a processing system for acquiring data based upon secondary electron emissions from the crystalline sample. The system may further include a crystalline standard for providing a channeling contrast reference.

In addition, a system for crystallography is described herein as including: a sample holder for holding a crystalline sample; a first ion source for generating a first ion beam; a scanning actuator for controlling the relative movement between the first ion beam and the crystalline sample, the scanning actuator being controllable for directing the first ion beam at desired areas of the crystalline sample; and an electron detector for detecting secondary electrons emitted from the crystalline sample. The system also includes: a first processing system for creating a contrast intensity image based upon secondary electron emissions from the crystalline sample; a second processing system programmed to provide crystallographic information based on the contrast image intensity data; and a controller for controlling the scanning actuator for scanning the first ion beam. The system may also include a second ion source for generating a second ion beam. The system may also include a crystalline standard for providing an ion channeling reference to the processing system.

A method for determining crystallography of bulk crystal sample is described herein as including: providing a sample holder for holding a crystalline sample for characterization of a sample area; generating an electron beam; controlling the relative movement between the electron beam and the crystalline sample to direct the electron beam at a series of spaced apart points within the sample area. The method also includes generating crystallographic data based upon electron diffraction from the crystalline sample; determining whether sufficient data have been acquired to characterize the sample area; and spacing the points apart such that acquired data is representative of a different grain within the crystalline sample.

A method for determining crystallography of bulk crystal sample is herein described as including: providing a sample holder for holding a crystalline sample; generating a first ion beam; controlling the relative movement between the first ion beam and the crystalline sample, for directing the first ion beam at desired areas of the crystalline sample; detecting secondary electrons emitted from the crystalline sample.

The method further includes creating a contrast intensity image based upon secondary electron emissions from the crystalline sample; providing crystallographic information based on the contrast image intensity data; and controlling the scanning actuator for scanning the first ion beam.

In addition, a method for determining crystallography of bulk crystal sample is described herein as including: providing a sample holder for holding a crystalline sample; generating a first ion beam; generating an electron beam; controlling the relative movement between the first ion beam, the electron beam, and the crystalline sample for directing the first ion beam at desired areas of the crystalline sample and for directing the electron beam at a series of points within the sample area. THE method also includes detecting secondary electron emissions from the crystalline sample; creating a contrast intensity image based upon secondary electron emissions from the crystalline sample and generating crystallographic data based upon electron diffraction from the crystalline sample; providing crystallographic information based on the contrast image intensity data and configured for determining whether sufficient data have been acquired to characterize the sample area; and controlling the scanning actuator to direct the first ion beam at desired areas such that each ion channeling image is representative of channeling directions within the crystalline sample and spacing the points apart such that acquired data is representative of a different grains within the crystalline sample.

BRIEF DESCRIPTION OF THE DRAWINGS

The features of the invention believed to be novel are specifically set forth in the appended claims. However, the invention itself, both as to its structure and method of operation, may best be understood by referring to the following description and accompanying drawings.

FIG. 6A depicts an example schematic scan line (SL) the present invention (FIG. 4).

FIG. 33A is a reflectivity image of a relatively rough tungsten sample having an inset area fraction legend.

FIG. 33B is reflectivity image of a relatively smooth tungsten sample having an inset area fraction legend.

DETAILED DESCRIPTION OF THE INVENTION

I. Inline Metrology System

Figure 1:
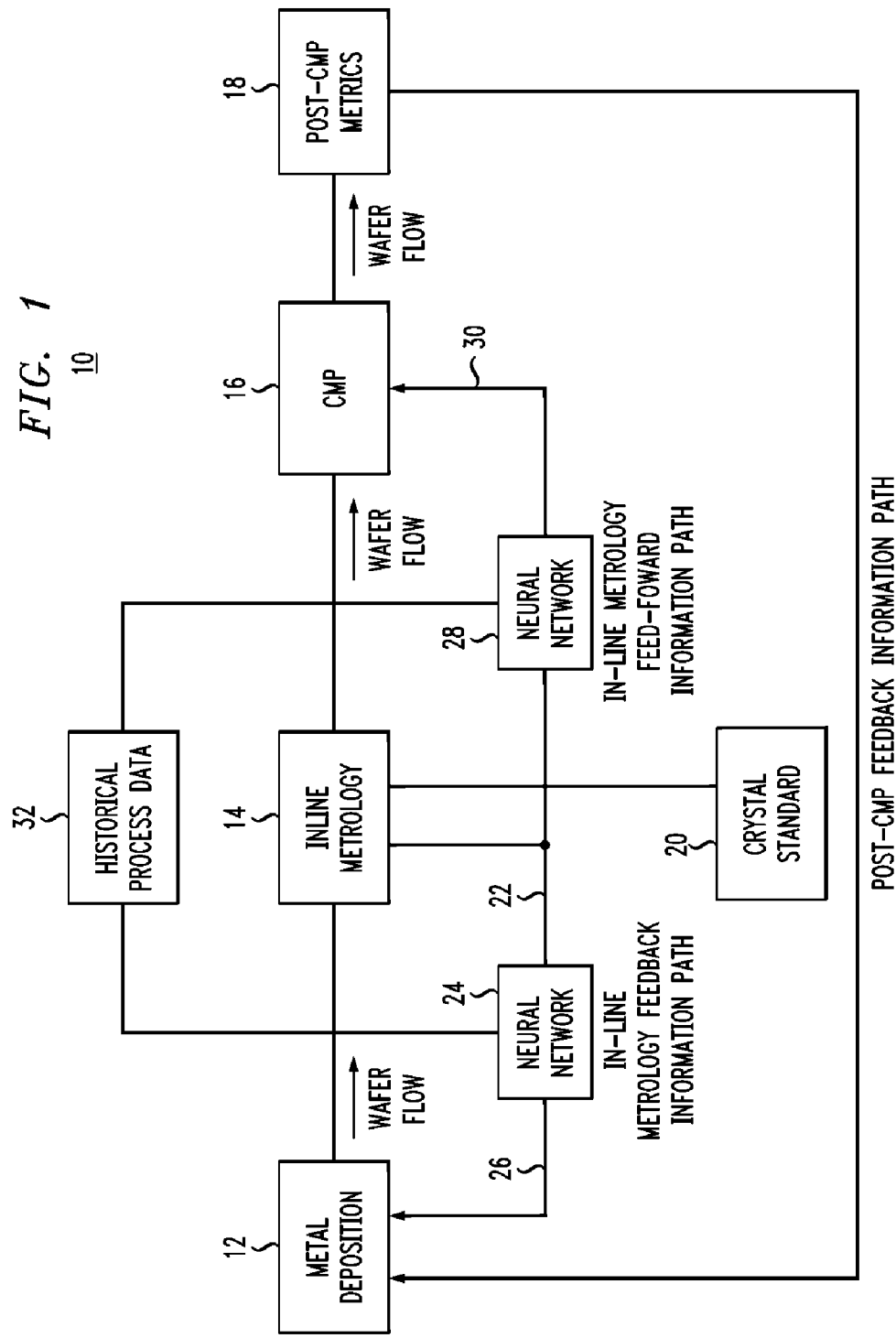
FIG. 1 is a block diagram illustration of a system for inline metrology and feed-forward/feedback control of a semiconductor process.

FIG. 1 illustrates a system 10 that may be used to implement a method for controlling a semiconductor device fabrication process. In an aspect of the invention, the system provides feed-forward and feedback in-line control of a metal deposition process and of a CMP process based on crystallography measurements of a processed semiconductor wafer. Advantageously, this system integrates the functions of metal deposition, inline metrology, and CMP processing to reduce overall process time and provide improved control over the device fabrication process. As a result, the system can produce an acceptable end product from a range of input morphologies that is broader than can otherwise be accommodated with prior art feed-back systems. In a further aspect to the invention, neural network algorithms may be provided in the in the feedback and feed forward loops to adaptively adjust feedback and feed forward data.

As depicted in FIG. 1, a semiconductor wafer is first processed through a metal deposition element 12 to form, for example, a layer of metal on the semiconductor wafer surface. The metal deposition element 12 may be any known metal deposition development system or method, such as a chemical vapor deposition (CVD) process or system. The wafer is then processed through an inline metrology element 14 to measure the geometry and quality of the deposited layer, such as the crystalline structure of the layer. The inline metrology element 14 may be any known apparatus or technique, and may preferably include developing a crystallography characterization of the semiconductor wafer using scanning electron microscope (SEM) or a focused ion beam (FIB) inspection data.

In the embodiment of FIG. 1, the inline metrology element 14 may provide a multiple parameter characterization of a wafer surface 22 as a feedback signal to the metal deposition element 12, for example to control the deposition, RF power, gas flow and other controllable parameters of the metal deposition process. The inline metrology element 14 may access a crystal standard 20 to index measurements performed on a wafer to establish an appropriate multiple parameter characterization of a wafer surface 22. In an aspect of the invention, the multiple parameter characterization of a wafer surface 22 may be provided as an input to a feedback neural network 24. The feedback neural network 24 may be trained by either self-organization or by supervised learning to provide a feedback control signals 26 to adaptively adjust parameters of the metal deposition process. In addition, feedback neural network 24 may be provided with historical process data 32 for the deposition process. Feedback neural network 24 is designed to find a mapping from multiple parameter characterization of a wafer surface 22 to parameters to achieve, for example, uniform crystal orientation by deposition of wafers in the CVD according to a respective crystallography of the wafer determined in the inline metrology element. A neural network is advantageously used to define the relationship between the multiple parameter characterization of a wafer surface 22 and, for example, an RF power used in the CVD process, since the amount of data available regarding the relationship between these two variables may be limited, and the level of understanding of that relationship may also be limited. As experience is added to the historical database 32 by the processing of wafers through system 10, the precision of this mapping operation will correspondingly improve.

After inspection in the inline metrology element 14, wafers may then be processed in a CMP element 10, for example any known CMP system or process. The multiple parameter characterization of a wafer surface 22 may be provided in feed forward loop to a CMP process, or in an aspect of the invention, as an input to a feed-forward neural network 28 in an inline metrology feed-forward information path. The feed-forward neural network 28 then provides a feed-forward control signal 30 to adaptively adjust parameters of the CMP process, such as amount of polishing chemical used, removal rate curves, and other adjustable parameters used in CMP processes. In addition, feedback neural network 24 may be provided with historical process data 32 for the deposition process. Feed forward neural network 28 is designed to find a mapping from multiple parameter characterization of a wafer surface 22 to parameters to achieve, for example uniform polishing of wafers according to a respective crystallography of the wafer determined in the inline metrology element. A neural network is advantageously used to define the relationship between the multiple parameter characterization of a wafer surface 22 and, for example, CMP removal rate curves, since the amount of data available regarding the relationship between these two variables may be limited, and the level of understanding of that relationship may also be limited. As experience is added to the historical database 32 by the processing of wafers through system 10, the precision of this mapping operation will correspondingly improve.

Figure 2:
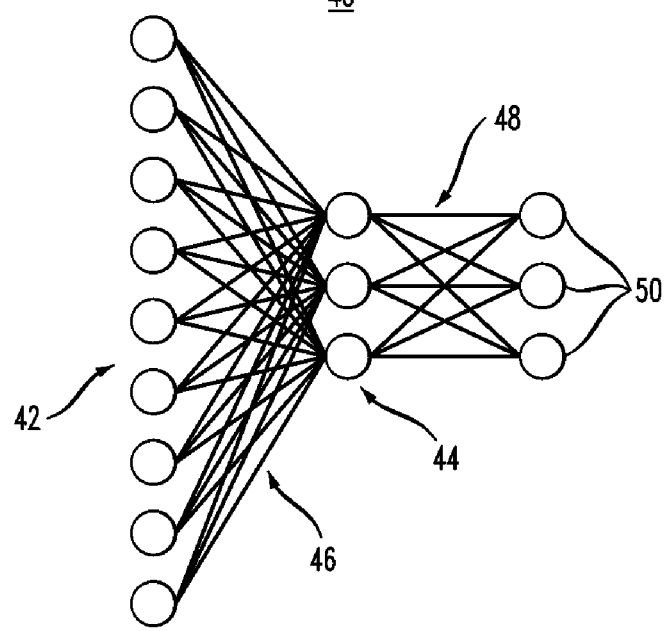
FIG. 2 is a schematic representation of a self-organized neural network.

Neural networks 24, 28 may be trained by any method known in the art, including by a self-organized learning algorithm of the type described in Kohonen, T., Self-organization and Associative Memory, Springer-Verlag, Berlin (1984). The Kohonen algorithm is just one of many self-organization algorithms (also known as competitive learning) that have been reviewed by Ballard, D. H. (1997), An Introduction to Natural Computation, MIT Press, Cambridge, Mass. and by Hassoun, M. H. (1995), Fundamentals of Artificial Neural Networks, MIT Press, Cambridge, Mass. A self-organized network 40 having input nodes 42 is illustrated in FIG. 2 and may be trained as follows. Assume the input vector is the multiple parameter characterization of a wafer surface 22. Let this vector be represented by the symbol M and let the output from the classification nodes 44 be represented by the symbol Y, and W will represent the connection matrix 46 between the input 42 and the classification nodes 44. The value for any given element in the Y vector is given by:

$$y_j = f\left(\sum_i W_{ij} x_i\right) \quad [1]$$

If one starts with small positive random numbers in the connection matrix W, then each classifier node will produce the same output value for the same input vector. The function f could be a simple logistic function, for example:

$$f(z) = \frac{1}{(1 + \exp(-z))} \quad [2]$$

With this algorithm one of the output vector elements will have a greater value than the others (e.g. $y_1 < y_2$ $y_1 < y_3$ $y_2 > y_3$). One may exploit the differences between the individual output vector elements for computational purposes by increasing or decreasing their values. In the example described, the second element is the largest value or the winner. But it is not necessary to determine explicitly which value is the largest or which is the smallest. One may simply use the following algorithm to update the weights between the input nodes and the classification nodes.

$$W_{ij}(t+1) = W_{ij}(t) + \delta W_{ij} x_i \quad [3]$$

The advantage of this algorithm is that there is no need to explicitly examine the classifier output. To determine if the network self-organization has converged, one may simply monitor the magnitude of the changes taking place in the connection matrix 46.

After training the network, one may find that the actual outputs for the classifier nodes are not as strong as preferred, but that they are differentiated from each other. It is possible to further enhance this difference by using a winner-take-all network 48 on the back-end of the self-organizing classifier. This can be done by using simple "If" statements to select the largest output, or by a MAX(y) function to arrive at output nodes 50. At this stage, the system 10 of FIG. 1 will provide a goodness class from the network and this represents, for example, the quality of the multiple parameter characterization of a wafer surface 22

Figure 3:
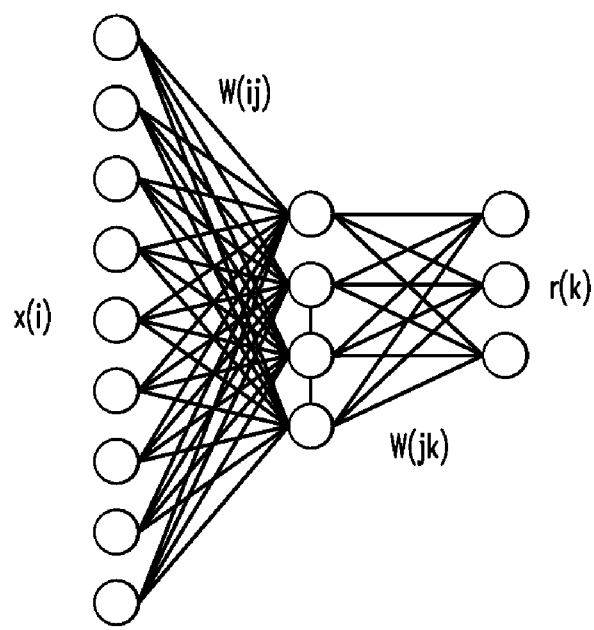
FIG. 3 is a schematic representation of supervised neural network architecture.

There may be and preferably are similarities in training the feedback neural network 24 and the feed-forward neural network 28. A supervised learning algorithm known as the back-propagation of errors can train both. This algorithm is well known in the art with many published papers describing it and its applications. Two published sources for the algorithm are Hassoun, M. H., Fundamentals of Artificial Neural Networks, MIT Press, Cambridge, Mass. (1995) and Reed, R. D. and Marks, II, R. J., Neural Smithing—Supervised Learning in Feedforward Artificial Neural Networks, MIT Press, Cambridge (1999). The following is a brief description of the training algorithm and how it may be applied to the present invention, as illustrated in FIG. 3.

The output of a neural network, r, is given by $$r_k = \sum_j \left[ W_{jk} \cdot \tanh\left( \sum_i W_{ij} \cdot x_i \right) \right]. \quad [4]$$

This equation states that the $i^{th}$ element of the input vector x is multiplied by the connection weights $W_{ij}$. This product is then the argument for a hyperbolic tangent function, which results in another vector. The resulting vector is multiplied by another set of connection weights $W_{jk}$. The subscript i spans the input space. The subscript j spans the space of "hidden nodes", and the subscript k spans the output space. The connection weights are elements of matrices, and are found by gradient search of the error space with respect to the matrix elements. The cost function for the minimization of the output response error is given by:

$$C = \left[ \sum_j (t-r)^2 \right]^{\frac{1}{2}} + \gamma \|W\|^2 \quad [5]$$

The first term represents the RMS error between the target t and the response r. The second term is a constraint that minimizes the magnitude of the connection weights, W. If γ (called the regularization coefficient) is large, it will force the weights to take on small magnitude values. This can cause the output response to have a low variance, and the model to take on a linear behavior. With this weight constraint, the cost function will try to minimize the error and force this error to the best optimal between all the training examples. The effect is to strongly bias the network. The coefficient γ thus acts as an adjustable parameter for the desired degree of the non-linearity in the model.

In order to apply this technique to training the feed forward neural network 28, for example, we use the multiple parameter characterization of a wafer surface 22 as the input vector X and a CMP removal rate curve, for example, as the output target value T. This discussion is provided for illustration only, and does not limit the application of this invention to other control parameters used in a CMP or CVD process. Similarly, the method described herein may be applied directly to other processes, such as an etch processes or photolithography processes. After selecting the input vector X and the target value T, the network 28 is then trained using the previously described well known algorithm and/or using the historical process data 32. The objective of network 28 is to compute a CMP removal rate curve for running a CMP process. The input to the neural network 28 is the multiple parameter characterization of a wafer surface 22 and the network 28 will model the process of mapping the multiple parameter characterization of a wafer surface 22 to the CMP removal rate curve. As additional data is accumulated, the connections in neural network 28 can be updated as the process changes, thereby helping neural network 28 adapt to real-world changes.

Accordingly, system 10 may be used for on-line automation of a semiconductor manufacturing process allowing for the selection of a control parameter values that will move a measured wafer geometry toward a target acceptance range. Such feed-forward and feedback control applies information acquired through in-process metrology to a downstream and an upstream manufacturing step, respectively. In an embodiment, the feed-forward and feedback controls are provided to the respective manufacturing steps via neural networks having as an input a multiple parameter characterization of the input device morphology. This integrated metal deposition-inline metrology-CMP process can adapt to changes in variables that may not be adequately monitored or whose impact may not be fully appreciated to adjust the process in response to the input profile and the desired after-etch profile.

II. Inline Metrology Elements

As described earlier, the inline metrology element 14 may include any known apparatus or technique, or combinations of apparatuses of techniques, and may include developing a crystallography characterization of the semiconductor wafer using scanning electron microscope (SEM) or a focused ion beam (FIB) inspection data. Advantageously, the invention provides a novel inline metrology system and method that measures crystallographic orientation, grain size, and grain morphology at faster speeds than conventional possible without the need for offline and/or destructive testing. As used herein, area fraction means the fractional percentage of a grain orientation along a polycrystalline material surface relative to a specified direction.

A. Scanning Electron Microscope (SEM)

Figure 4:
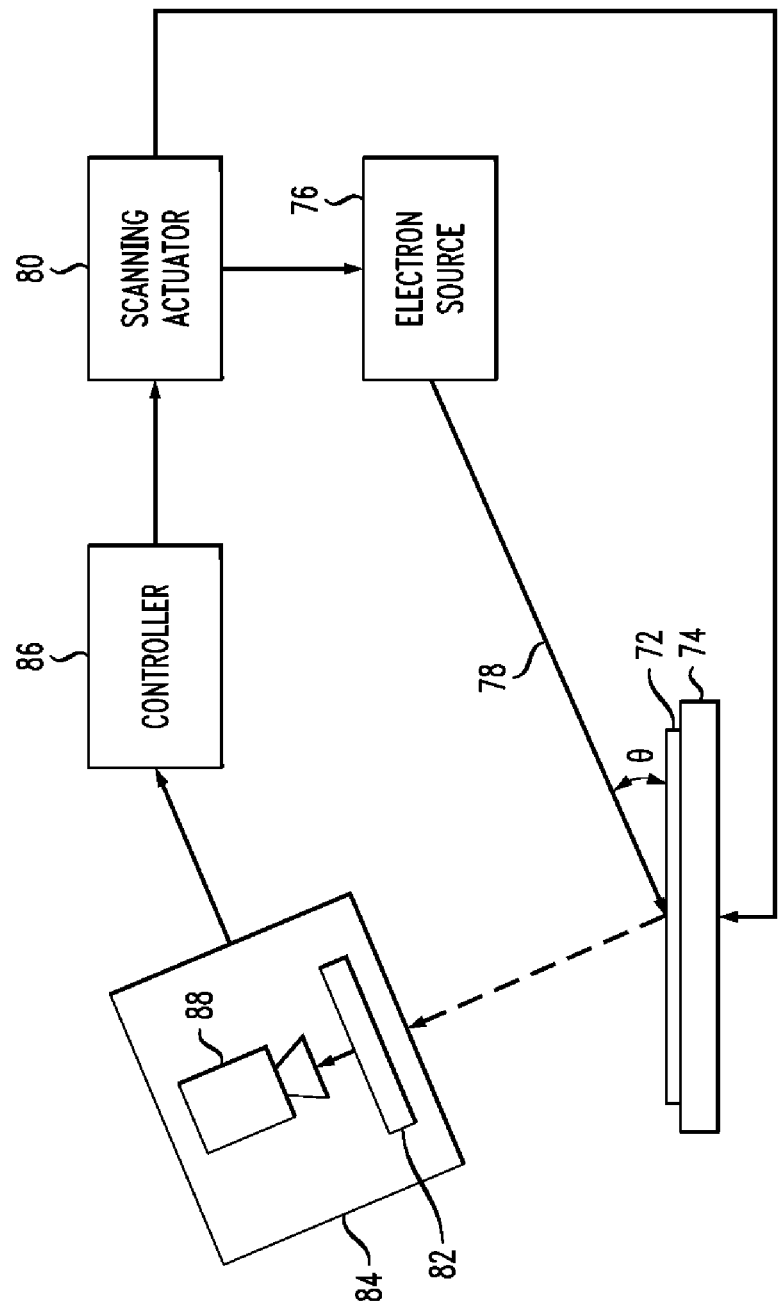
FIG. 4 shows an embodiment of an inline metrology element including an electron source for scanning a crystalline sample.

Referring now to FIG. 4, an embodiment of an inline metrology element 70 for scanning a crystalline sample 72, such as a copper film deposited on a semiconductor wafer, will now be described. The metrology element 70 includes a sample holder 74 for holding the sample 72 at a glancing angle θ to an electron beam 78. The electron beam 78 is generated by an electron source 76. A scanning actuator 80 is provided for controlling relative movement between the electron beam 78 and the crystalline sample 72 on the sample holder 74. The scanning actuator 8 is controllable for directing the electron beam 78 at a series of spaced apart points of the crystalline sample 72. In other words, the scanning actuator 80 may control movement of the electron source 76 to move the electron beam 78 relative to the sample 72 on the sample holder 74, or the scanning actuator may control movement of the sample holder relative to the electron beam, or both.

An processing system, such as an image processor 84, is provided to process images formed on a phosphor screen 82, e.g., by intensifying and/or amplifying the images. The image processor 84 may comprise a low light or charged coupled device (CCD) camera 88 to capture the images. The phosphor screen 82 is mounted adjacent the sample holder 74 so that it is parallel to the incident electron beam 78. Diffracted electrons from the sample 72 form images on the phosphor screen 82. These images are known as Kikuchi diffraction patterns and include Kikuchi bands, which can be used to determine the crystallographic grain orientation at a point within a scan area of the sample 72. The pattern center is preferably located near the top of the phosphor screen 82 for maximum band formation.

The image processor 84 mathematically decomposes the Kikuchi diffraction pattern through a Hough transform to identify the band structure, as is well known to those skilled in the art. See, for example, U.S. Pat. No. 6,326,619. The geometrical symmetry of the band structure is used to determine the crystallographic grain orientation of the crystalline sample at the current point. A controller 86 compares the crystallographic grain orientation at the current point with the crystallographic grain orientation from a previous point. The electron beam 78 or the sample holder 74 is then stepped to the next point and the process is repeated. The stepping occurs in a raster pattern with a predetermined step size over the entire scan area.

The crystallographic grain orientation of a crystal phase varies within a narrow tolerance. This tolerance is typically less than the noise exhibited by the Hough transformation conversion to angular spacing between crystal planes. Therefore, only a single determination of the crystallographic grain orientation is needed for each point. In one aspect, the step size or spacing between sample points is set such that each point is taken from a different grain within a scan area of the crystalline sample 72. The term "step size," as used in the disclosure is the distance between consecutive points of a sample at which the electron beam 18 is directed for grain orientation analysis.

The step size may be greater than a "known grain size" of the crystalline sample and/or at least as large as a "known grain size." The term "grain size," as used in this disclosure, refers to that measurement of a grain using techniques known to those skilled in the art, e.g., an intercept method (ASTM Test Method E 112) or planimetric method (ASTM Test Method E-2) or other methods. For a description of such test methods, see Vander Voort, "Committee E-4 and Grain Size Measurements: 75 Years of Progress," ASTM Standardization News (May, 1991).

The known grain size may be characterized as a standardized grain size for a particular crystal phase of the crystalline and may be obtained from publications listing standardized grain size for various materials. One such publication is The Journal of Vacuum Science and Technology. The step size for operation of the present invention is a function of grain size, such as ten times the grain size.

Figure 5:
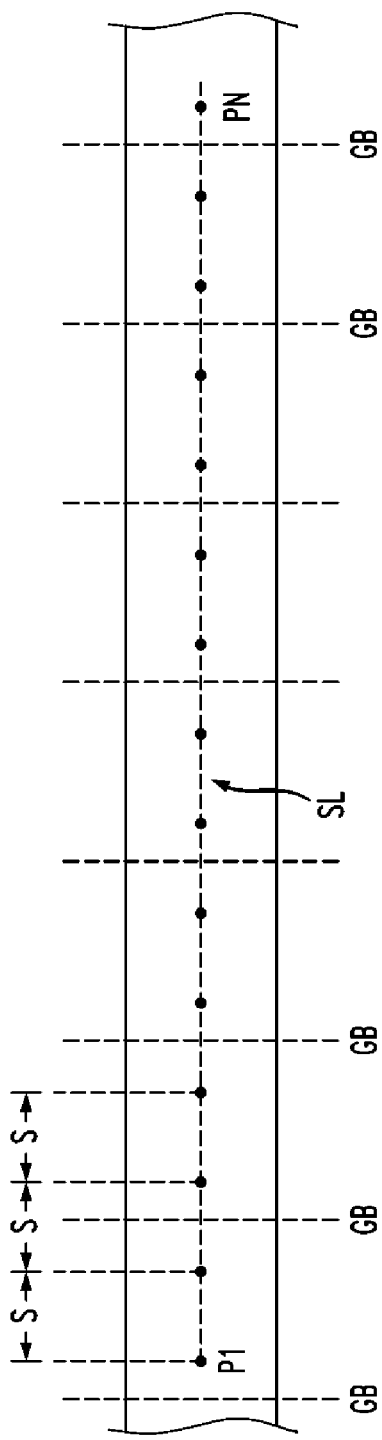
FIG. 5 depicts an example schematic scan line (SL) of the prior art.

Referring to FIGS. 5 and 6A, example schematic scan lines (SL) of the prior art (FIG. 5) and the present invention (FIG. 6A) are now compared. Each of the scan lines depicted in FIGS. 5 and 6 is schematically represented as a straight line. The scan lines disclosed in FIGS. 5 and 6A herein represent a series of spaced apart points taken from a sample and may follow any preselected pattern, a random pattern, and may have any desired spacing distance. In the present invention, for example, a first point may be randomly selected within a scan area of the sample 72; and the next point may be spaced apart at a distance that is at least as large as a known grain size of the sample 72. A preselected direction with respect to consecutive points is not critical to the operation of the present invention, but it is preferred to obtain grain orientations of different grains of the sample within a scan area.

The prior art scan line SL of FIG. 5 includes spaced-apart points P1-PN where data is taken. The points P1-PN are spaced apart by a fixed step size S, e.g., 50 nanometers. Grain boundaries (GB) exist within this sample scan line SL and, as illustrated, the number of data points P1-PN is fixed, based on the fixed step size S.

The scan line SL illustrated in FIG. 6A, according to the present invention, includes spaced apart points P1 through P7 where data is taken. Grain boundaries (GB) exist between grains (G1 through G7), within the sample scan line SL, but the spacing between points is increased to reflect a point taken from a different grain within a scan area of the sample 72. For example, the spacing between each of the points P1 through P7 is twice the size of the grains G1-G7. In this manner, a grain orientation analysis can be taken from a different grain within the scan line for each given point.

Figure 7:
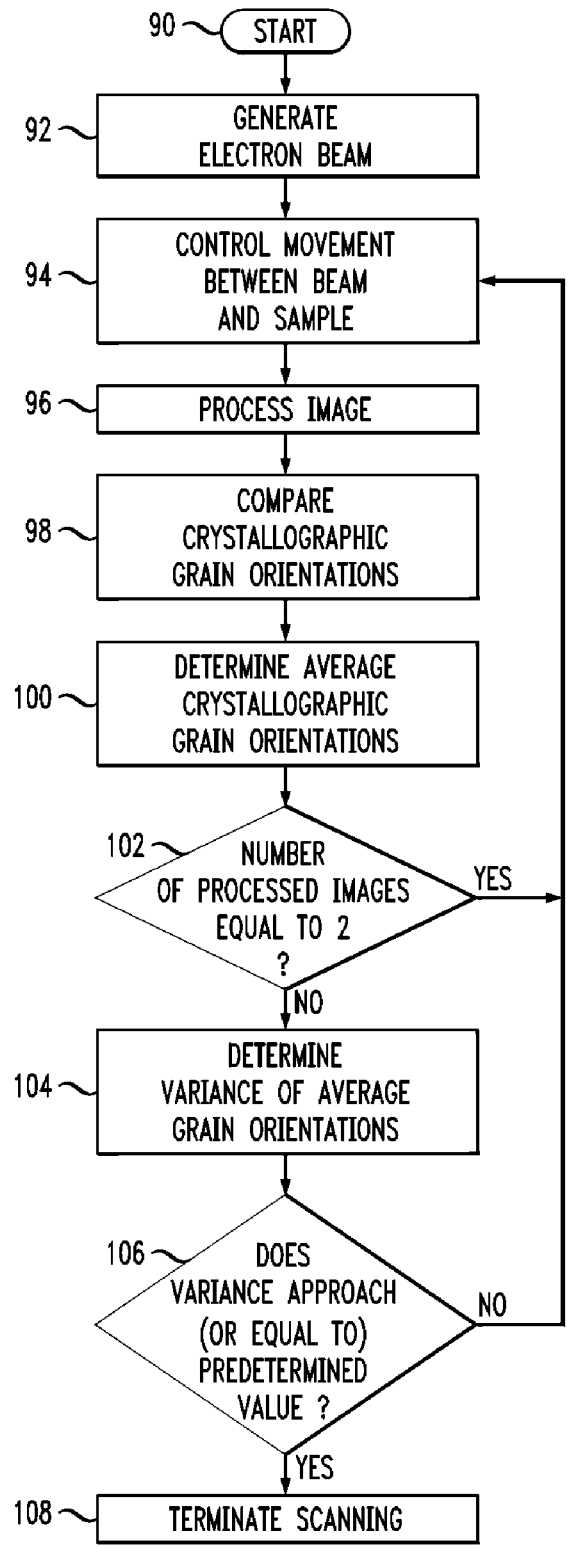
FIG. 7 is a flow chart of the basic steps of a method for scanning a crystalline sample.

Referring to FIG. 7, the basic steps of the method for scanning a crystalline sample 72 in accordance with the present invention are now described. In accordance with the present invention, the method begins (Block 90) and the sample 72, e.g., a copper film deposited on a semiconductor wafer, is held at a glancing angle to an electron beam 78. For example, the sample 72 may be held by a sample holder 74 or stage, as shown in FIG. 4, in a substantially horizontal position. Preferably, the glancing angle θ is about 20 degrees. At Block 92, an electron beam 78 is generated at the sample 72 and at Block 94, the relative movement between the sample 72 and the Block 94 is controlled to direct the electron beam at a series of spaced apart points of the crystalline sample.

Diffracted electrons from the crystalline sample 72 define an image, which is processed (Block 96), e.g., by an image processor which preferably includes a low light camera or a CCD camera. The image may be formed on a phosphor screen 82 and comprises a Kikuchi diffraction pattern. The step of processing the image (Block 96) may include converting the Kikuchi diffraction pattern to a Hough space to identify the Kikuchi bands at a current point within the crystalline sample 72. Also, the step of processing the image (Block 96) may include determining a crystallographic grain orientation at the current point within the crystalline sample 72 based on the Kikuchi bands.

The method preferably includes a step (Block 98) of comparing the crystallographic grain orientation from the current point with the crystallographic grain orientation from a previous point. At Block 100 an average grain orientation between the current point and the previous point is determined. For example, with respect to FIG. 5, if the grain orientation of P1 is (1,1,1) and the grain orientation of P2 is (0,0,1), the average grain orientation is the vector that bisects the direction vectors of the (1,1,1) and (0,0,1) planes.

At block 102, if the average grain orientation of only two points has been taken, then the crystallographic grain orientation for a third point must be determined. Once a grain orientation for a third point, P3 (FIG. 6) is taken, it is compared to the grain orientation of points P1 and P2. At Block 100, an average grain orientation for points P1, P2 and P3 is determined to be, for example. In the next step (Block 104), the controller 96 determines a variance between average grain orientation for points P1-P2 and an average grain orientation calculated for points P1, P2 and P3.

At Block 104 a variance between the average grain orientation determined for points P1 and P2 is compared to the average grain orientation for points P1, P2 and P3, to determine a variance in average grain orientation. The term "variance," as used in this disclosure, shall include a variance or standard deviation in average grain orientations, which variance and/or standard deviations are calculated from a statistical analysis of the data comparing grain orientations and/or average grain orientations. The mathematical formulas are well known to those skilled in the art.

In the next step (Block 106), the variance in the average grain orientation of the sample 72 is compared to a predetermined value. If the variance approaches, or is equal to, the predetermined value the scanning is terminated at Block 108. If the variance is not approaching, or equal, to the predetermined value the scanning of the sample 72 continues to the next point. The scanning process is repeated for points P4 and P5. The variance in grain orientation is monitored during the scanning procedure, or until the variance approaches, or is equal to, the predetermined value, at which step (Block 108), the scanning is terminated. Typically, the predetermined value will be zero.

A benefit of the method of the present invention is that it provides faster collection. In accordance with the method, the number of data points within a grain structure can be decreased where points taken at a step size, for example, larger than a known grain size of the crystalline sample is needed. An adequate sample of data is collected for evaluation of the crystalline sample, in a minimal amount of time. With respect to fabrication of semiconductor devices, the crystallographic grain orientation of each of respective scan points can be used to calculate a preferred grain orientation of the sample, which calculation is well known to those skilled in the art.

Figure 6B:
FIG. 6B depicts exemplary concentric circle scan lines superimposed over a crystalline sample.

FIG. 6B depicts exemplary concentric circle scan lines superimposed over a crystalline sample. In another aspect of the invention, a statistical method of determining grain size based upon optical methods may be used by adapting it to the electron beam tool and applying a scan method whereby the beam is directed to move in either concentric circles or a series of lines and the grain boundaries counted. The ratio of the number of grain boundaries to the size of the concentric circles or length of the lines can be used to make a statistical determination of grain size. The novel aspect of this invention is in utilizing the electron beam tool with a step size small enough to be able to distinguish grain boundary locations along a series of circles or lines. The mathematical methods for determining the statistical grain size from the number of events is known to one skilled in the art.

Accordingly, an electron beam system using variable scan methods can provide statistical orientation and statistical grain size of a crystalline sample. Because of the greatly reduced time frame for collection, this method can be used inline to determine grain size and crystallographic information.

B. Single Focused Electron Beam (FIB)

Figure 8:
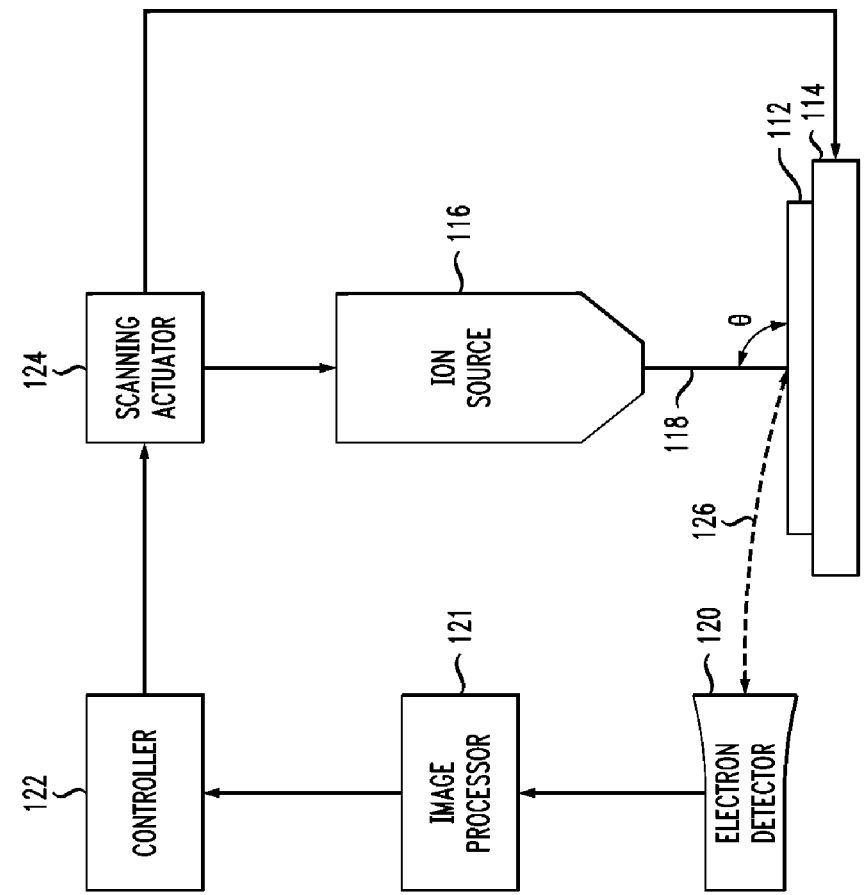
FIG. 8 depicts an ion beam embodiment of an inline metrology element for scanning a crystalline sample.

Referring now to FIG. 8, an ion beam embodiment of an inline metrology element 110 for scanning a crystalline sample 112, will now be described. The metrology element 110 includes a sample holder 114 for holding the sample 112 at an angle θ to an ion beam 118. In an aspect of the invention, the angle is 90 degrees from the face of the crystalline sample 112 to be aligned with the fiber texture orientation so that crystals of similar orientation are detected with similar intensities. The ion beam 118 is generated by an ion source 16, such as a focused ion beam (FIB). In another aspect of the invention, the angle θ can be approximately 85 degrees from the face of the crystalline sample 112 so that the an ion beam 118 is not aligned with the fiber texture orientation. In this angular configuration, crystals of similar orientations are detected with varying intensities so that the boundaries can be identified.

A scanning actuator 124 is provided for controlling relative movement between the ion beam 118 and the crystalline sample 112 on the sample holder 114. The scanning actuator 124 is controllable for directing the ion beam 118 at selected areas of the crystalline sample 112. In other words, the scanning actuator 124 may control movement of the ion source 116 to move the ion beam 118 relative to the sample 112 on the sample holder 114, or the scanning actuator may control movement of the sample holder relative to the electron beam, or both. An electron detector 120 is provided to detect electrons 126 emitted from the surface of the sample 112 as the ion source 116 scans the ion beam 118 across the sample 112. In an aspect of the invention, the electron detector 120 is mounted perpendicular to the ion beam 118 near the edge of sample as shown in FIG. 8.

An image processor 121 may be provided to process contrast images received by the electron detector 120, e.g., by intensifying and/or amplifying the images. Once an image has been processed for a specific area, a controller 122 provides a control signal to the scanning actuator 124 to move the ion beam 118, or the sample holder, 114 to another desired area of the sample 112.

As is known in the art, electron emission from a crystalline material varies according to the statistical likelihood of a collision between and incident ion and a nucleus of a sample surface. The closer the distance to the surface where the nucleus impact occurs, the more intense the emission of secondary electrons from the surface. In a crystalline material, the likelihood for collision near the surface is reduced along, aligned areas of the crystal structure, or channeling directions. That is, the ion beam penetrates further in a channeling direction than a non-channeling direction.

An FIB instrument utilizes a finely focused ion beam, for example, from a Ga liquid metal ion source (LMIS) to perform imaging operations. The interaction of the finely focused ion beam with the target material will produce the ejection of secondary electrons, secondary ions, and secondary neutrals. The ions and neutrals can be ejected as individual atoms, molecules, or clusters. The imaging capability of the FIB allows the use of either the secondary electrons or the secondary ions for image formation.

Figure 9:
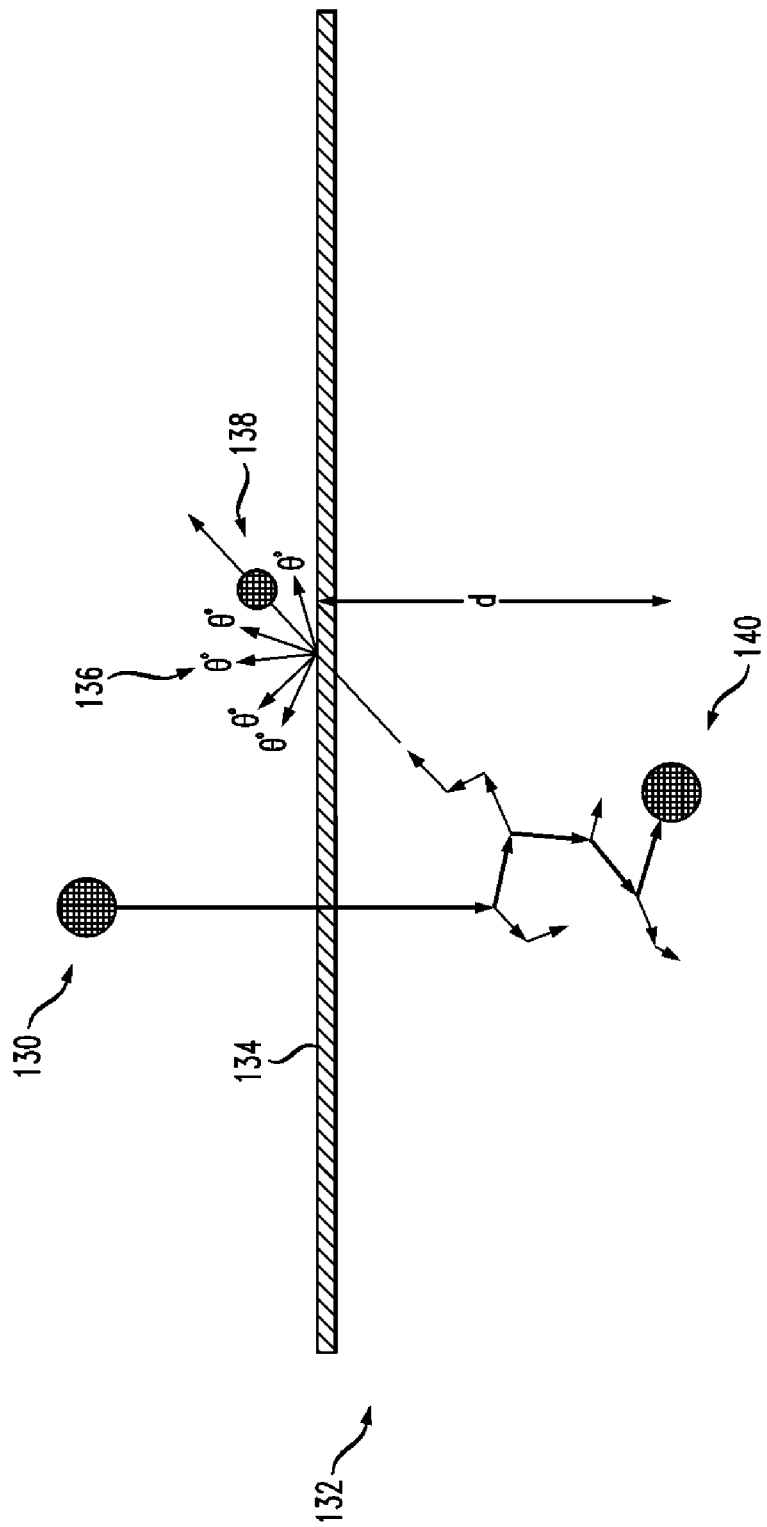
FIG. 9 depicts secondary electron emission and sputtering from a target material subject to an ion beam.

FIG. 9 depicts secondary electron emission and sputtering from a target material subject to an ion beam. It is well known that an incident ion 130, upon impact with a target material 132, will produce a collision cascade in the target material 132. If a surface atom receives enough of a normal component of momentum from the collision cascade to overcome a surface binding energy of the target material 132, surface atoms, such as a sputtered particle 138 leave a surface 134 of the target material 132. The factors that affect sputtering include the atomic number, energy, and angle of incidence of the ion beam, the atomic density of the target material 132, surface binding energy of the target material 132, and crystallographic orientation of the target material 132. In addition, the incident ion 130 will also generate secondary electron 136 emission form the surface of the target material 132. This secondary electron 136 emission is a function of the depth of penetration of the incident ion 130. Therefore it is possible to determine the approximate depth of penetration of an incident ion by examining the intensity of the generated secondary electrons 136 being emitted from the sample surface.

Figure 10:
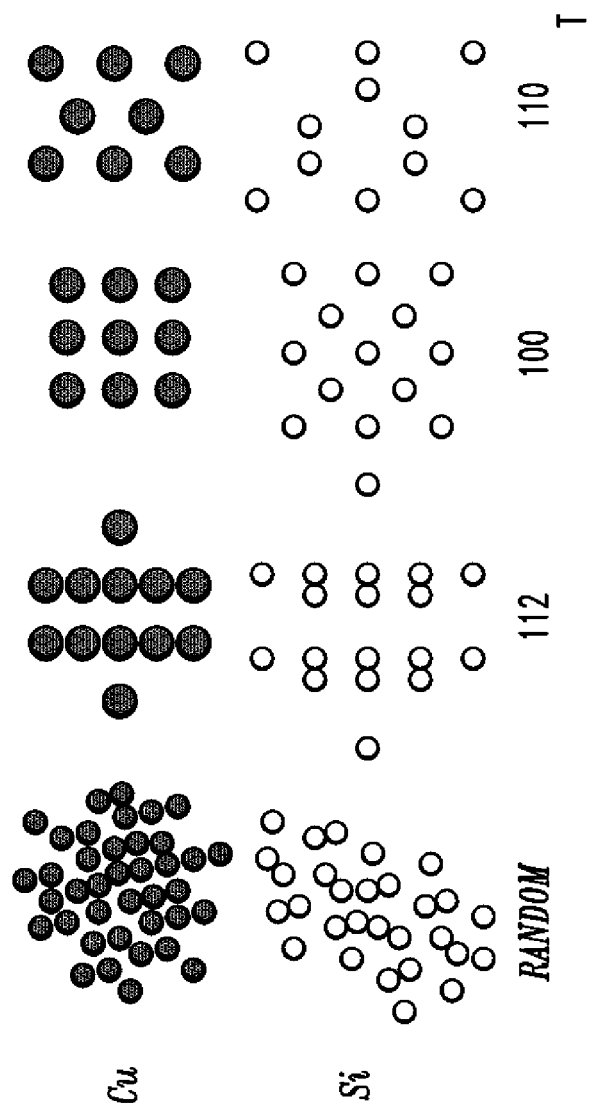
FIG. 10 shows a graphical representation of the primary channeling directions of copper and silicon in a random structure, and crystalline structures having Miller indices of <112>, <100>, and <110>, respectively.

FIG. 10 shows a graphical representation of the primary channeling directions of copper and silicon in a random structure, and crystalline structures having Miller indices of <112>, <100>, and <110>, respectively. The incident ions statistical depth is a function of the packing density of the cross sectional area of the depth of penetration. Therefore, for axial channeling directions where there are wider atomic channels, the primary ion will penetrate deeper into the sample surface and therefore generate less secondary electron emission from the top of a sample surface. For directions not coincident with channeling directions, there is a greater statistical probability of the collision of an incident ion with the nucleus of the sample surface and therefore, there will be greater amount of electrons emitted for sample directions not coincident with the channeling direction of the sample surface.

Figure 11:
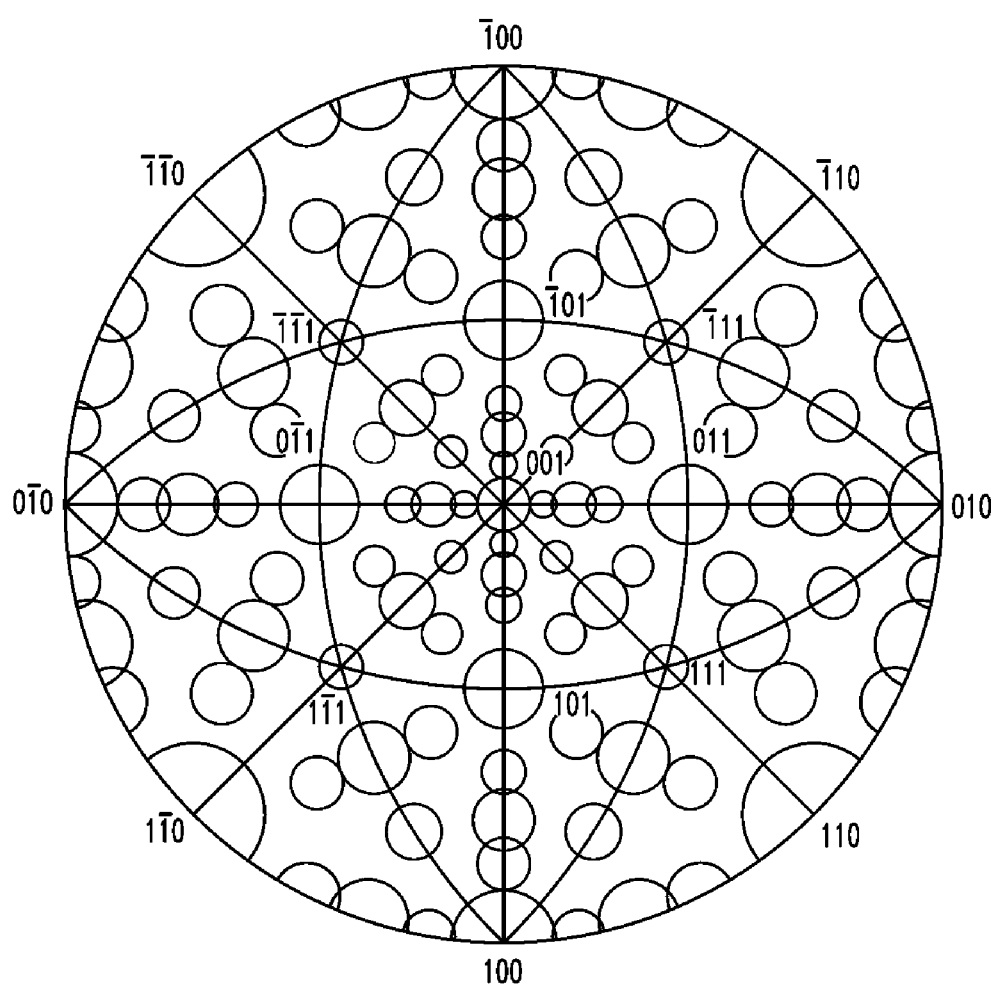
FIG. 11 shows a channeling map for 001 copper.
Figure 12A:
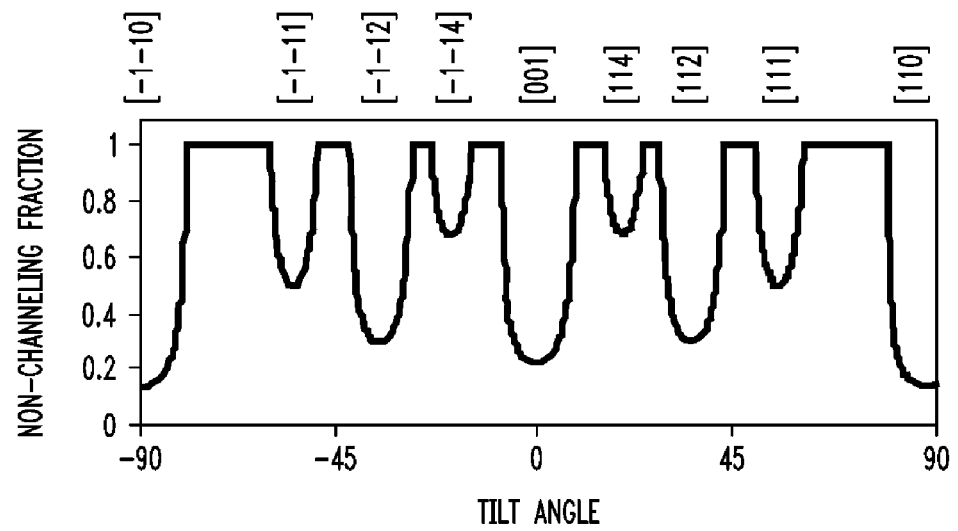
FIG. 12A shows a contrast intensity graph plotting tilt angle versus non-channeling fraction for 001 copper having a Miller index of <110>.
Figure 12B:
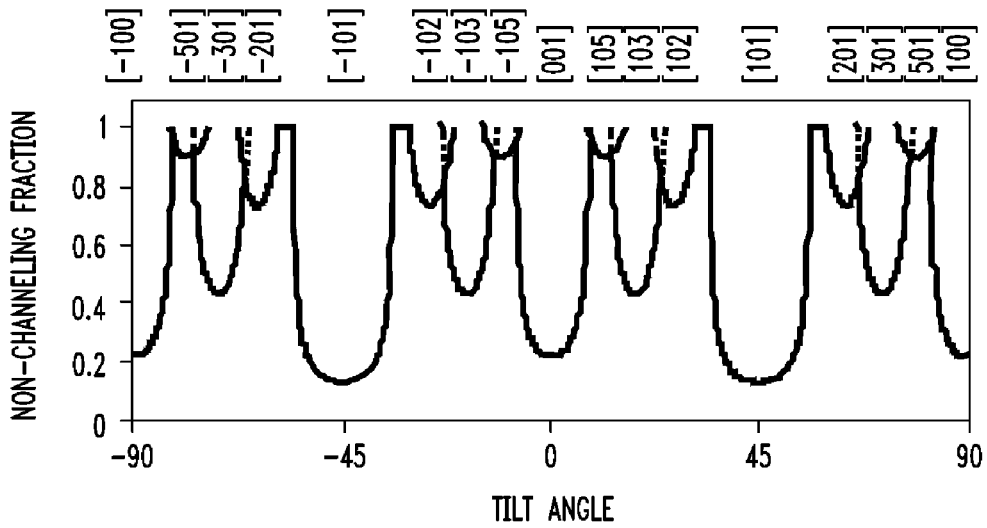
FIG. 12B shows a contrast intensity graph plotting tilt angle versus non-channeling fraction for 001 copper having a Miller index of <100>.

FIG. 11 shows a channeling map for 001 copper. The map depicts the effective channel widths for a primary direction and secondary direction within the copper. Analysis along a particular direction of the channeling map of FIG. 11 provides the contrast intensity graphs of FIGS. 12A and 12B. Accordingly, FIGS. 12A and 12B show contrast intensity graphs plotting tilt angle versus non-channeling fraction for 001 copper having a Miller indices of <110> and <100>, respectively.

Therefore, because of the crystal channeling, the FIB can be used to produce ion channeling contrast plots from secondary electron images captured by an electron detector recording the intensity of the secondary electron emission in polycrystalline samples. Ion channeling contrast occurs because the secondary electron yield varies as a function of crystallographic orientation within the sample. Channeling can occur when a crystallographic axis of a particular grain is aligned with the incident ion beam. As a result, that grain will appear darker due to a decrease in the number of secondary electrons that are produced. Advantageously, the ion channeling contrast can be interpreted to determine the orientation of the crystals in the a sample.

As the ion beam 118 is scanned across the surface to the sample 112, relatively fewer electrons will be emitted from the sample 112 when the ion beam 118 intersects a channeling direction, and a relatively greater number of electrons will be emitted when the ion beam intersects non-channeling directions. Therefore, both the orientation of the sample 112 with respect to the incident ion beam 118 as well as the channeling directions in the sample 112 affect the emission of electrons 126 from the sample 112 surface.

Accordingly, as the electron detector 120 detects the electrons 126 emitted from the sample 112, the emission intensity is provided to the controller 122 to correlate the emission intensity with a targeted location on the sample 112. Using the corrected emission intensity and targeted location information, a contrast map of the sample's 112 corresponding to crystalline channeling areas in the sample 112 can be created. The resulting contrast map can be used to determine the crystallographic grain orientation at a point within a scan area of the sample 112. In an embodiment of the invention, the contrast map developed using an FIB, for example, can be used to monitor processes and provide process control by taking advantage of the fiber texture nature of semiconductor metals.

To demonstrate the capabilities of ion channeling contrast in determining crystallographic orientation, several examples are provided herein. In addition, corresponding comparisons to known SEM techniques for determining crystallographic orientation is also provide for validation of the process.

Figure 13A:
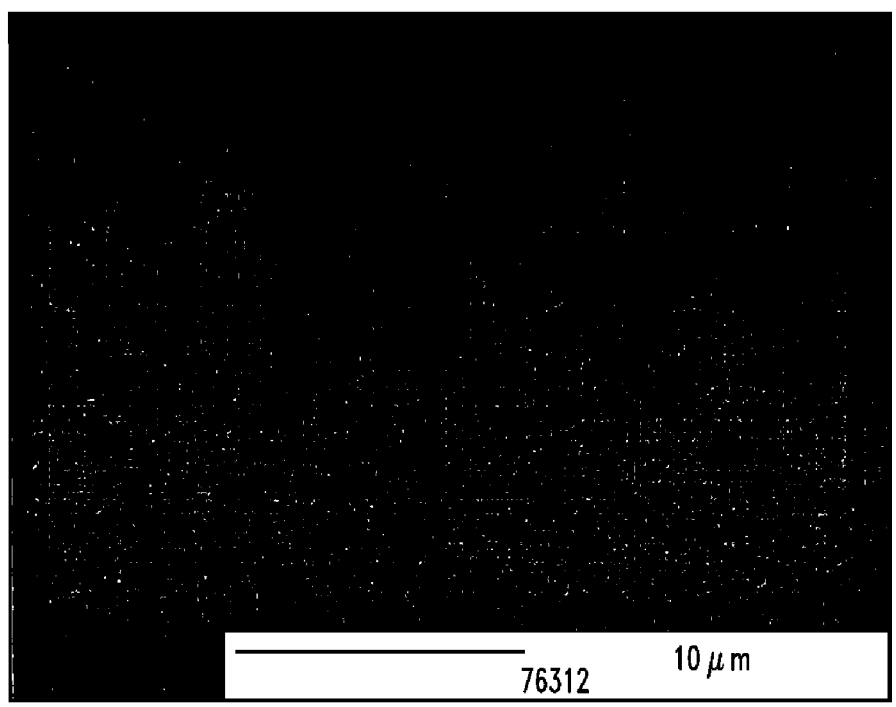
FIG. 13A is an FIB image of a nominal aluminum film of approximately 1 degree (full width half maximum) FWHM about the times random fiber texture orientation.

FIG. 13A is an FIB image of a nominal aluminum film of approximately 1 degree (fill width half maximum) FWHM about the times random fiber texture orientation, the image having a scale of 10 micrometers. Typically aluminum has strong fiber textural orientation of 111. Therefore, the primary direction of <111> is noted and changes in orientation are reflected as movements away from the channeling direction of 111, that is, the image shows more contrast away from a channeling direction due to a larger likelihood of collision between an incident ion and nuclei of the sample surface. The image appears to have all the same contrast except for certain areas which appear slightly brighter, These areas are the grain boundaries where the disorder at the boundary has created a localized increased likelihood of nuclear collision using, for example, an FIB.

Figure 13B:
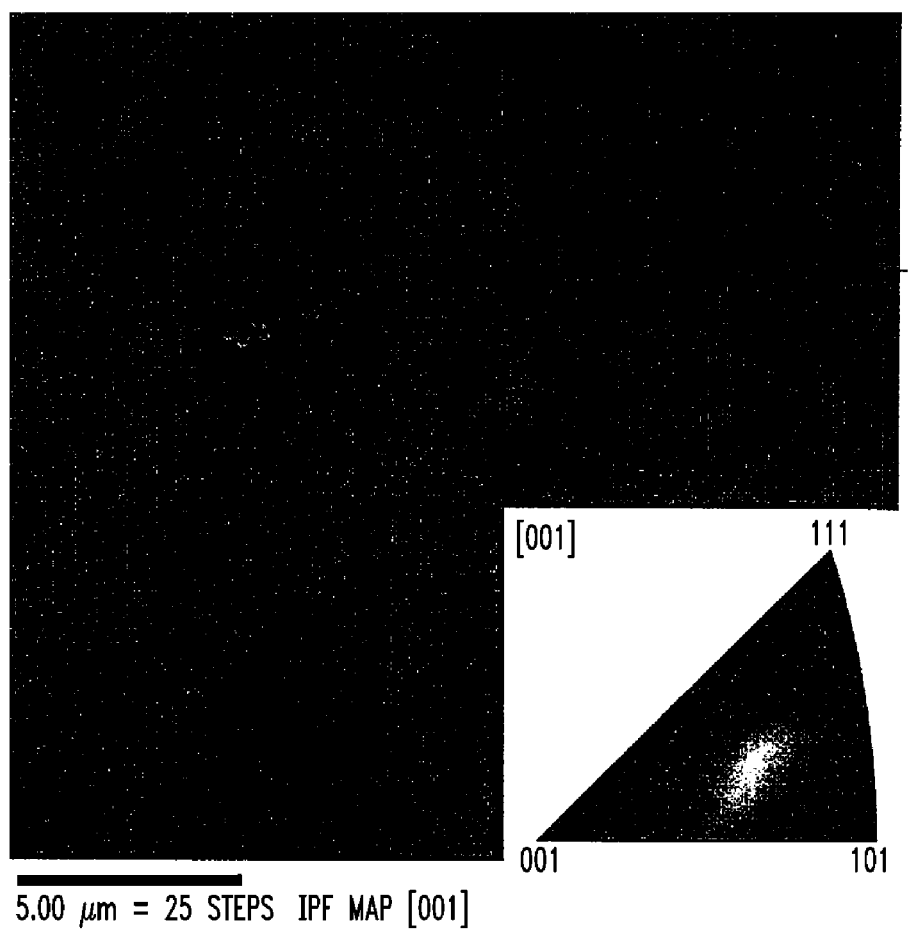
FIG. 13B is an electron diffraction image the same aluminum sample of FIG. 13A.

FIG. 13B is an electron diffraction image the same aluminum sample of FIG. 13A, the image having a scale of 5 micrometers. Inset in the lower right corner of the image is an inverse pole figure legend 142 wherein the gray shading corresponds to an automatic tiling function, as known in the art, of the unit triangle of the inverse pole figure. For example, the upper right portion of the inverse pole figure legend 142 is assigned a <111> crystal direction, the lower right portion is assigned a <101> crystal direction and the lower right portion is assigned a <001> crystal direction. Accordingly the gray scaling of the image corresponds to crystal direction according to the defined directions of the inverse pole figure legend 142. As can be seen, virtually the entire image corresponds to a crystal direction of <111>.

Figure 14:
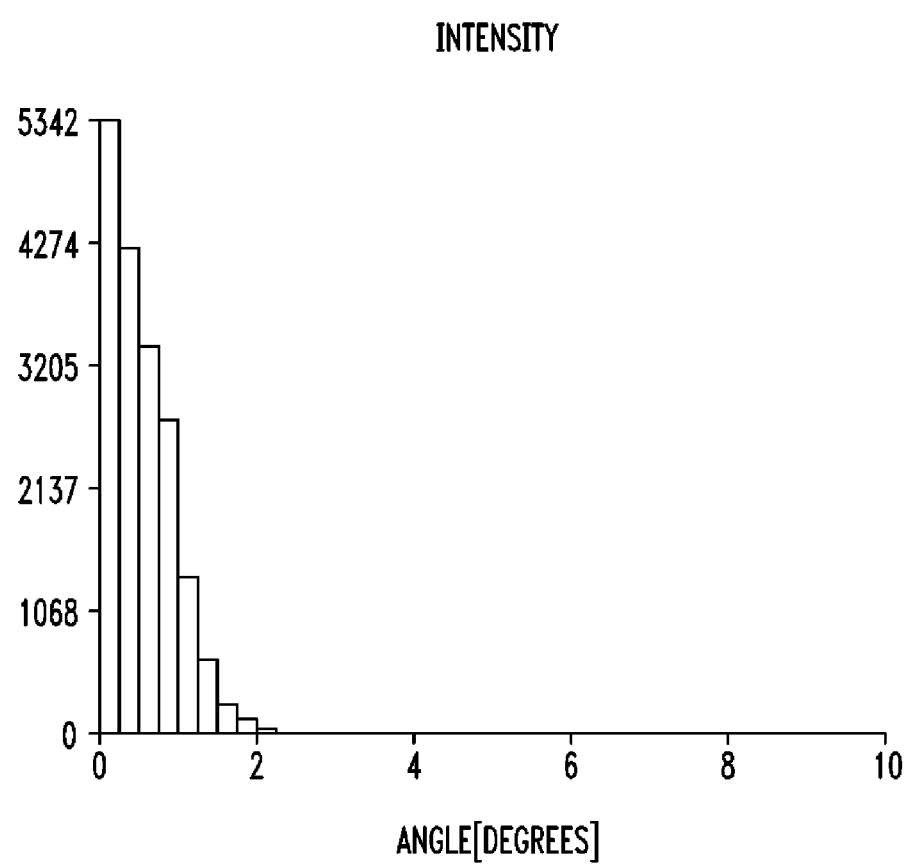
FIG. 14 shows a pole plot chart for the 111 aluminum sample of FIG. 13A.
Figure 15:
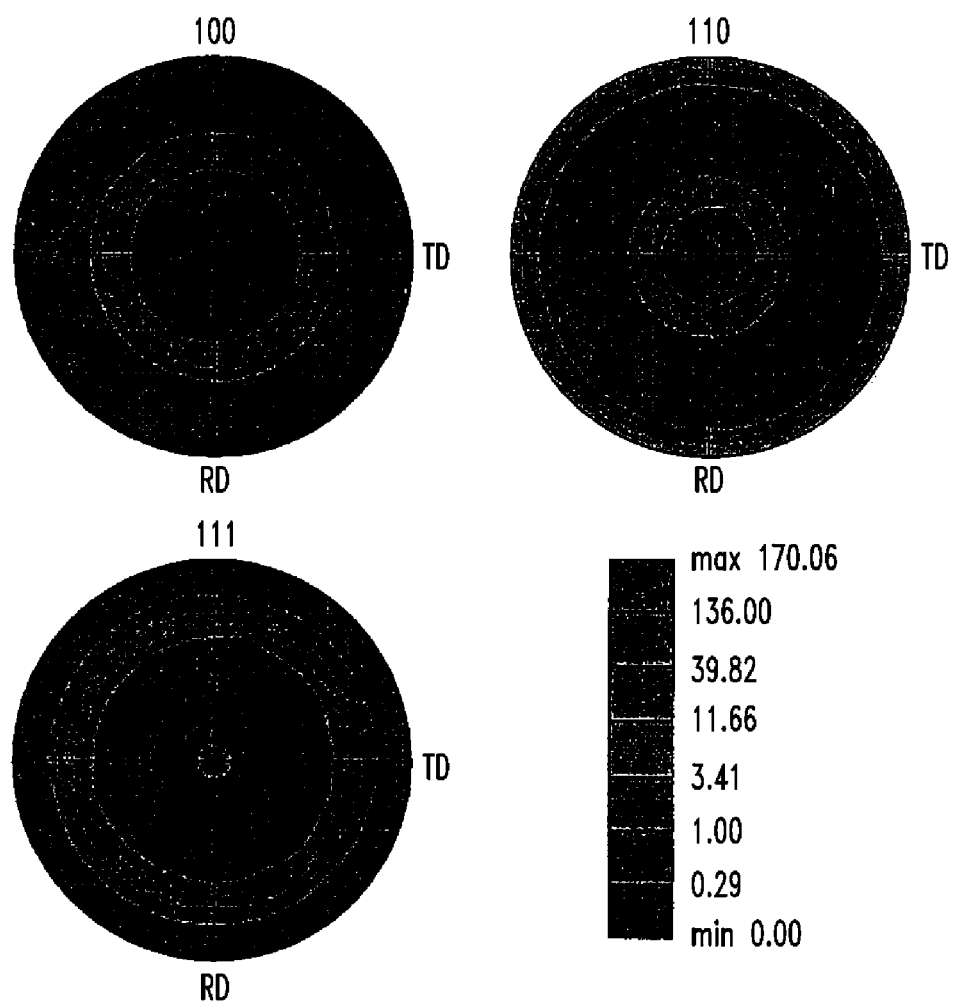
FIG. 15 shows pole figure plots for the 111 aluminum sample of FIG. 13A.

FIG. 14 shows a pole plot chart for the <111> aluminum sample of FIG. 13A. The pole plot chart can be generated from the electron diffraction information to analyze the times random component of the <111> orientation of the aluminum sample. The pole plot shows both the randomness of the sample in along rolling and transverse directions, the two directions in the plane of the wafer, and the relative strength of he fiber texture orientations. For example, the pole to be plotted is specified by entering the hkl Miller index for the desired lattice plane of interest. From the pole plot, it is evident from the steep drop off from the 0 degree angle axis that the imaged aluminum sample exhibits extremely tight textural orientation.

The pole plot also shows a the position of a pole (a normal to the lattice plane) relative to a sample reference plane. For example, the pole to be plotted is specified by entering the hkl miller index for the desired lattice plane of interest. The pole figures are a means of identifying preferred orientations within a polycrystalline sample. As shown, a tight, well formed circle in the <111> direction pole figure plot 144 indicates a strong orientation in the <111> direction.

Figure 16A:
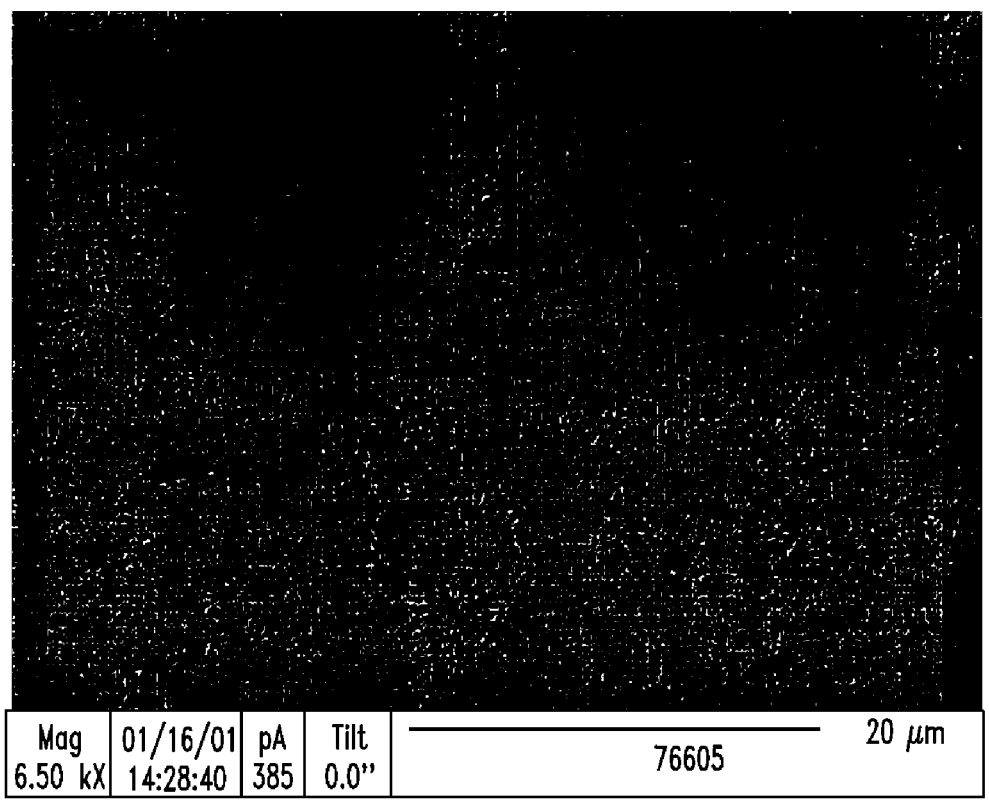
FIG. 16A is an FIB image of a defectively processed aluminum film.

FIG. 16A is an FIB image of a defectively processed aluminum film, the image having a scale of 10 micrometers. The process used to treat the aluminum film omitted a barrier step resulting in a weaker fiber texture of the defectively processed sample. Accordingly, the image exhibits a noticeable contrast differential caused by the weaker fiber texture. Advantageously this demonstrates that the FIB imaging process can detect problems caused by mistakes in barrier steps as well a metallization steps.

Figure 16B:
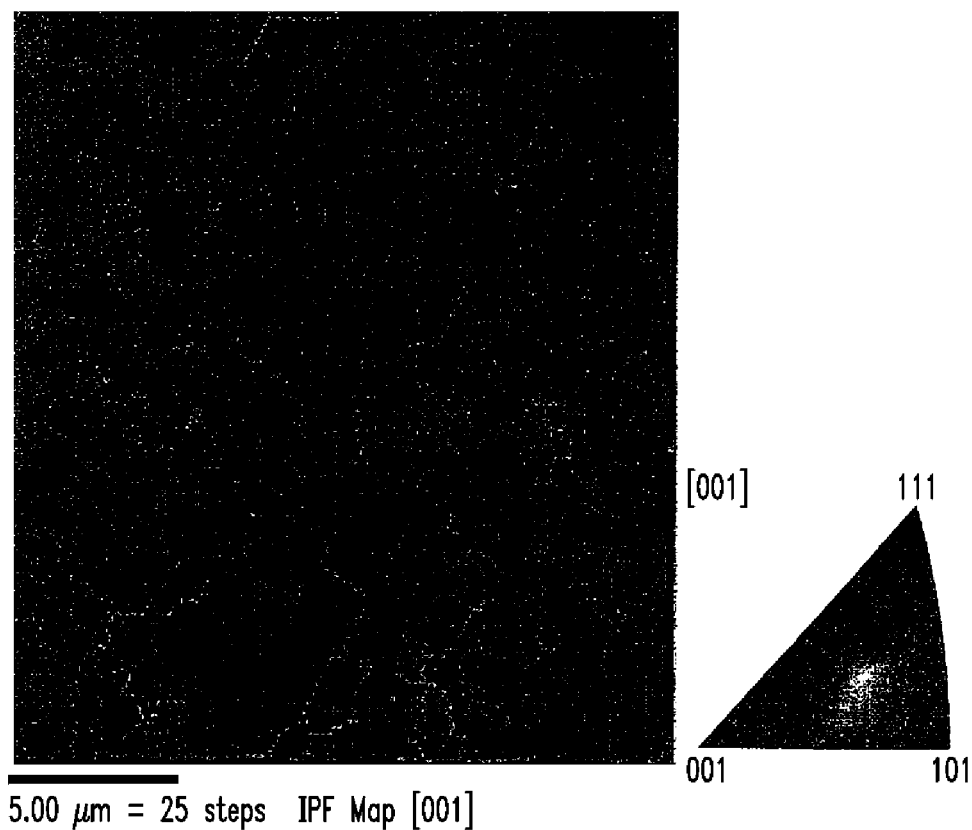
FIG. 16B is an electron diffraction image of the same aluminum sample of FIG. 16A.

FIG. 16B is an electron diffraction image of the same aluminum sample of FIG. 16A, the image having a scale of 5 micrometers, and including an inset inverse pole figure legend 146. The diffraction image exhibits crystal asymmetries as indicated by the lighter colored areas 148 in the images, thereby validating the FIB image obtained.

Figure 17:
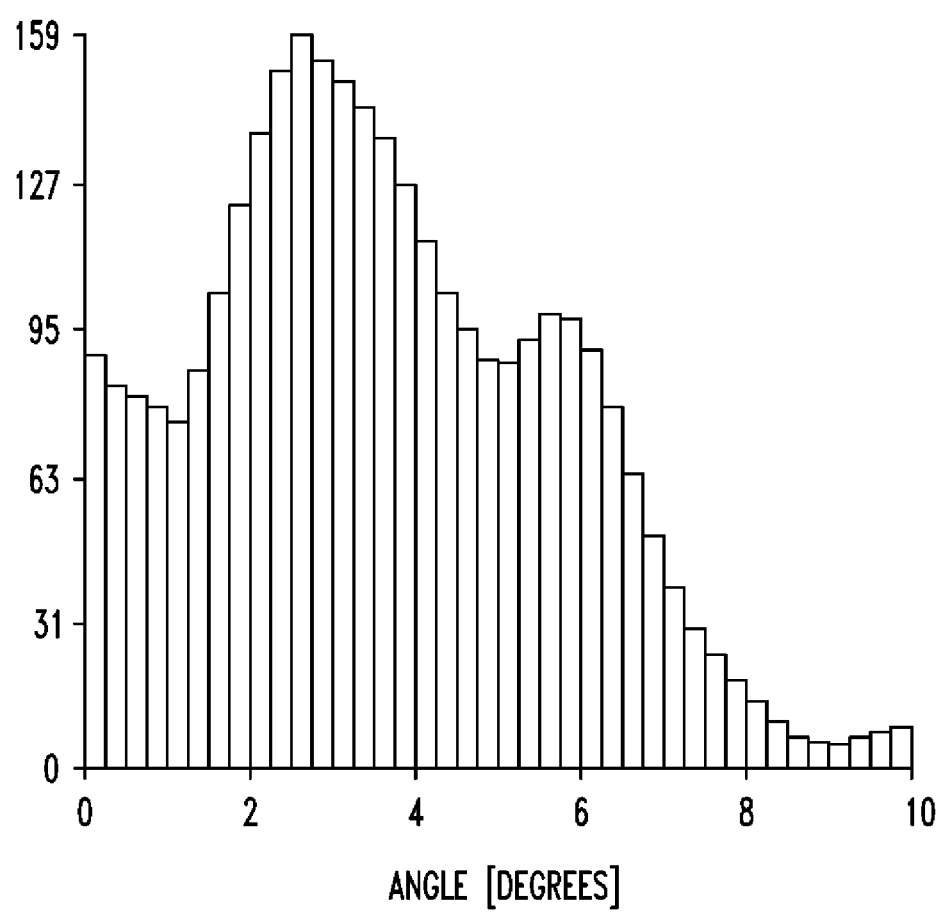
FIG. 17 shows a pole plot chart for the aluminum sample of FIG. 16A.

FIG. 17 shows a pole plot chart for the aluminum sample of FIG. 16A. The pole plot chart shows a far weaker fiber textural orientation as exhibited by the spread of the poles away from a 0 degree angle reference. This weakened fiber textural orientation can result in lowered mean time failure (MTF) rates in aluminum metallization.

Figure 18:
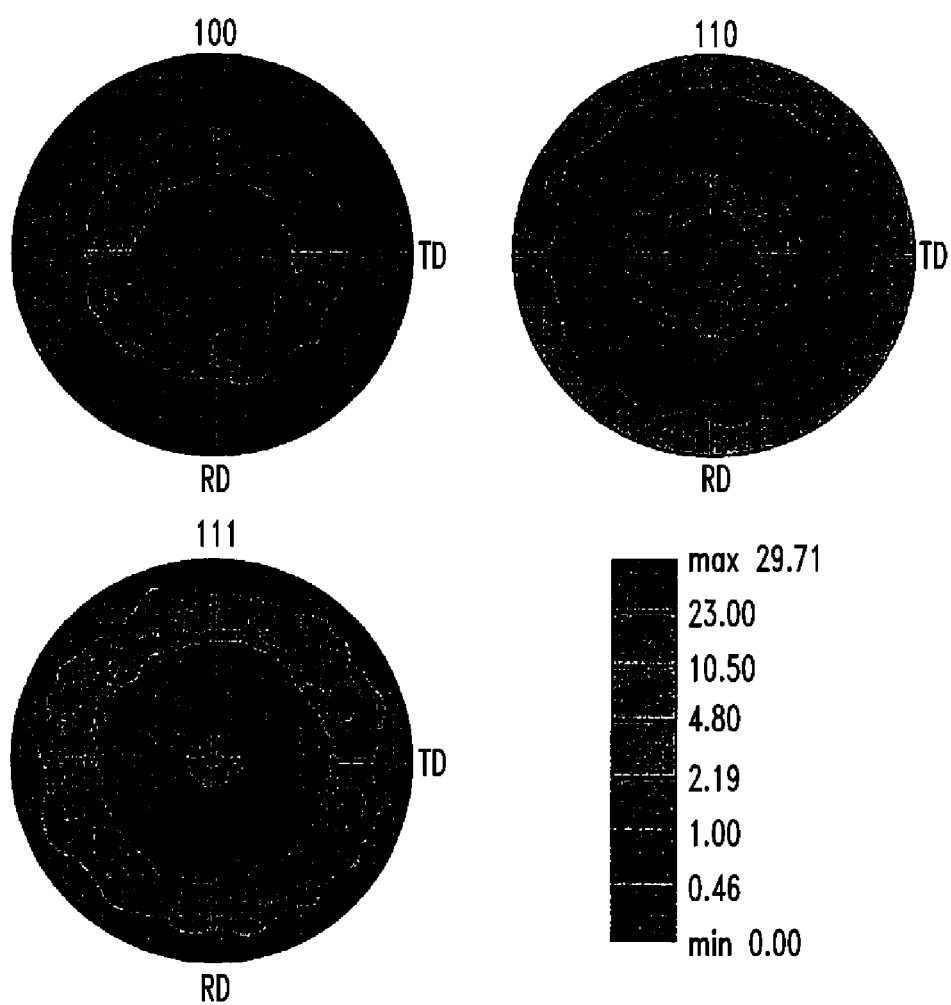
FIG. 18 shows pole figure plots for the aluminum sample of FIG. 16A.

FIG. 18 shows pole figure plots for the aluminum sample of FIG. 16A. As shown, misshapen, loose diffraction circles in the pole figure plots further indicate a weak fiber orientation in the aluminum sample of FIG. 16A. Accordingly, the electron backscatter diffraction data validates that the orientation of fiber textural material can be demonstrated using FIB channeling contrast images.

Figure 19A:
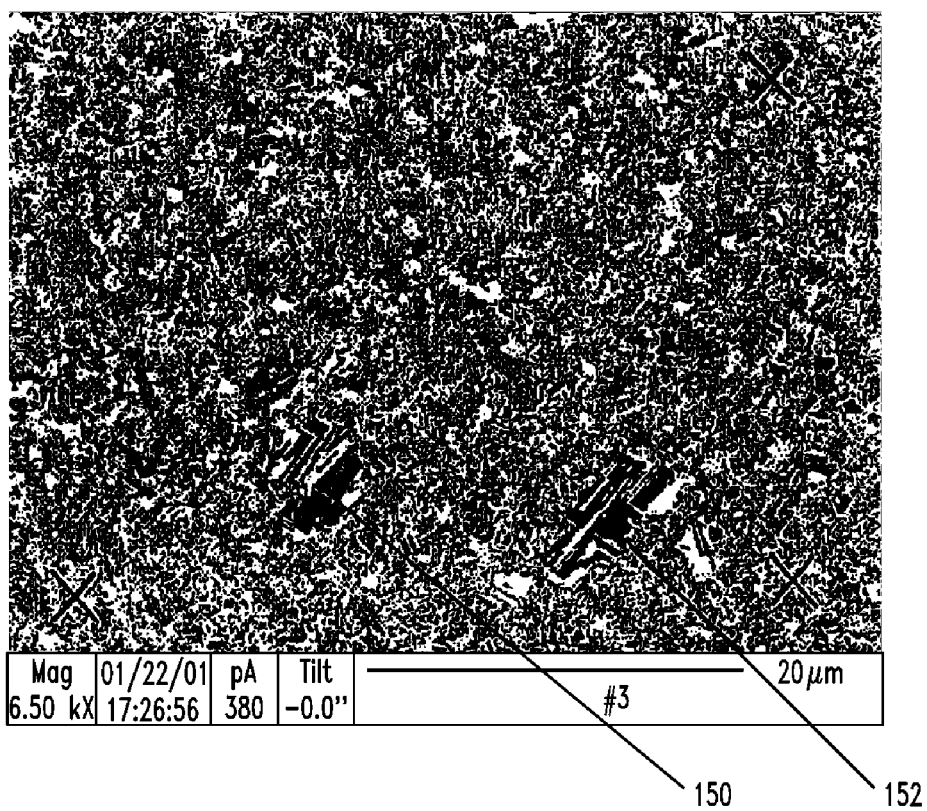
FIG. 19A shows an FIB image for a blanket copper seed layer.

Turning now to an example of a copper seed layer, FIG. 19A shows an FIB image for a blanket copper seed layer, the image having a scale of 20 micrometers. For copper seed layers, it is known that there is electromigration resistance for <111> copper (Cu) as compared to other orientation normals. The FIB image of FIG. 19A comprises primarily gray areas indicating a <111> orientation in the copper seed layer. The smaller areas of increased whiteness or blackness within the image are "three sigma" annealing twins of the <111> Cu. The two darker grains 150, 152 near the bottom of the image are grains having an appreciably different orientation than the rest of the sample.

Figure 19B:
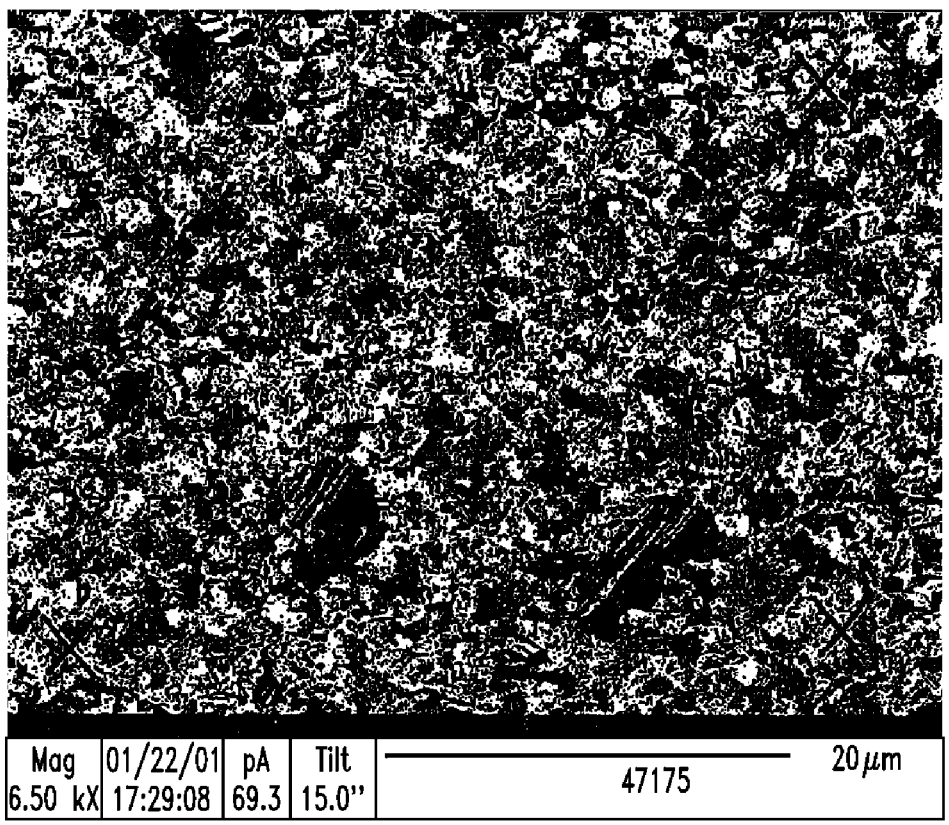
FIG. 19B shows another FIB image of the blanket copper seed layer of FIG. 19A, wherein the FIB has a different incident angle.

FIG. 19B shows another FIB image of the blanket copper seed layer of FIG. 19A, wherein the FIB has a different incident angle. As shown, by using a an incident ion angle that is not coincident with the central axis of the fiber texture of an imaged sample, the grain size can be easily identified and calculated.

Figure 20:
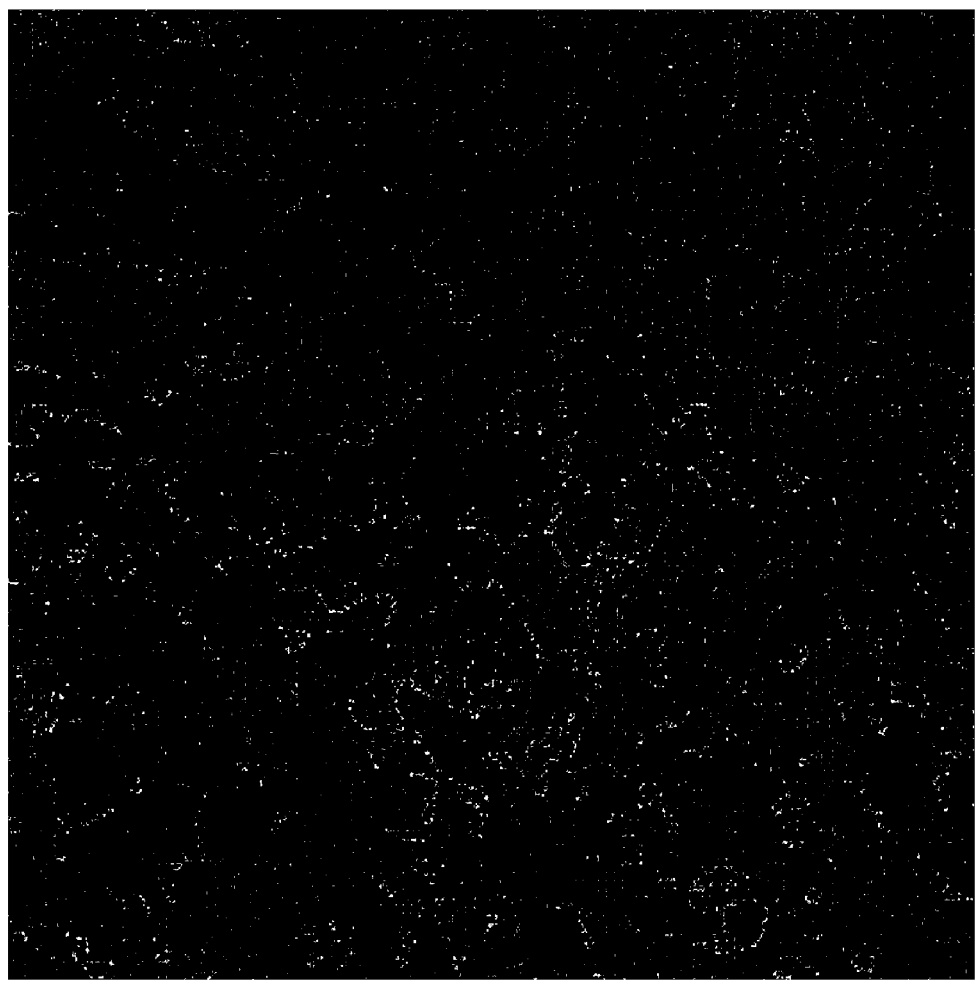
FIG. 20 is an electron diffraction image of the same copper seed layer of FIG. 19A

FIG. 20 is an electron diffraction image of the same copper seed layer of FIG. 9A, the image having a scale of 4.5 micrometers. The electron diffraction image reveal a mostly <111> orientation, as expected, with some grains having an off-axis orientation. The bulk of the copper seed layer having an <111> orientation is imaged as black, while the three sigma boundaries that are the annealing twins of the <111> Cu are imaged as lighter areas.

Figure 21:
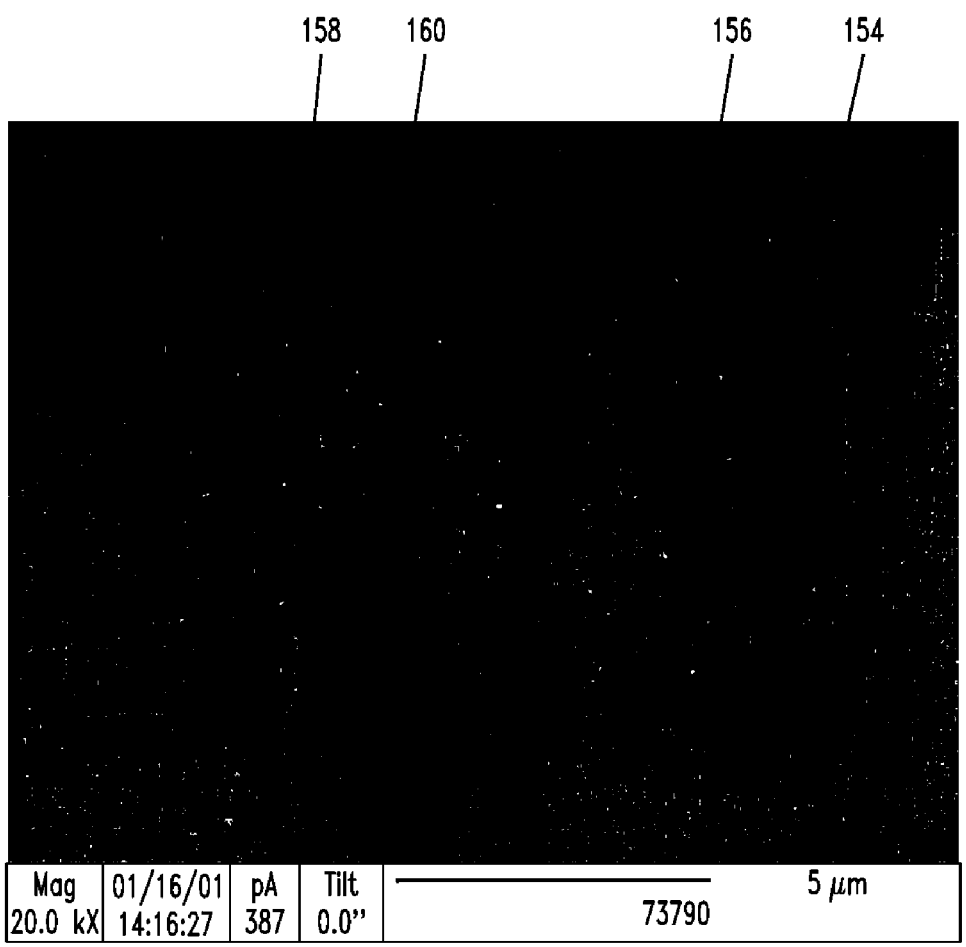
FIG. 21 shows an FIB image for a partially CMP'd tungsten layer.
Figure 22:
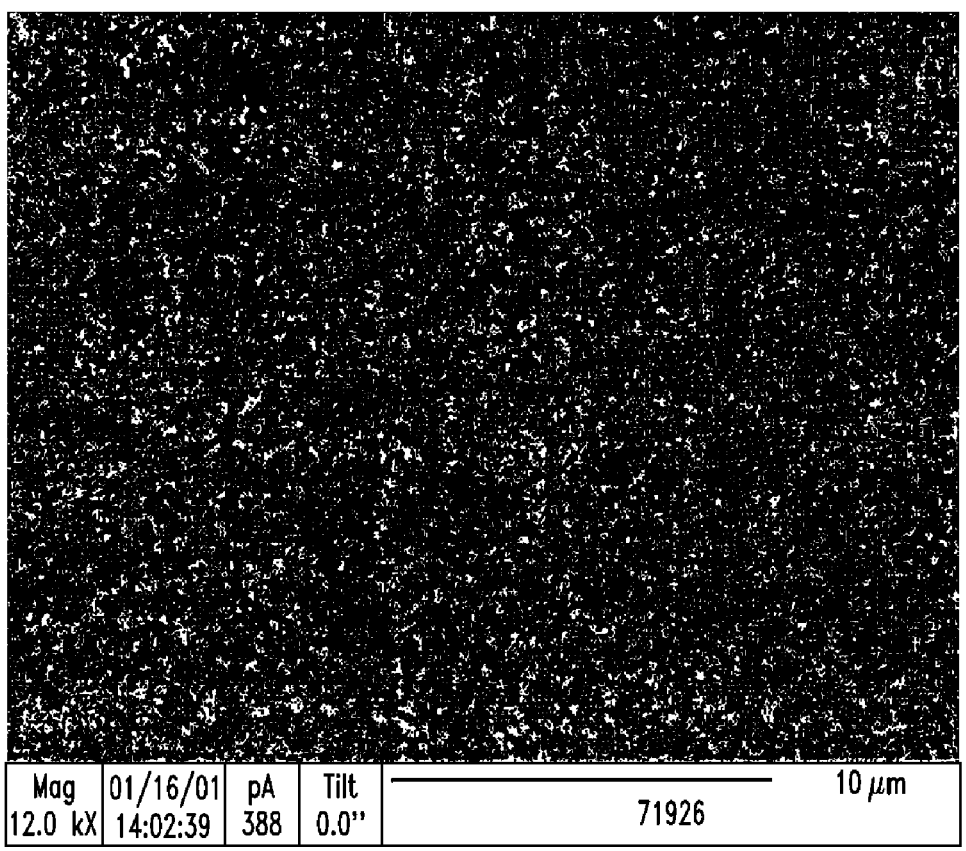
FIG. 22 shows an FIB image for a tungsten layer.

Turing now to a comparison of tungsten imaging using FIB and SEM techniques, FIG. 21 shows an FIB image for a partially CMP'd tungsten layer, the image having a scale of 5 micrometers. The darker areas 154, 156 correspond to areas of 110 orientation, while the overall lighter areas 158, 160 correspond to 114 orientation, as verified by electron backscatter diffraction. Of particular note for a CMP process, the 114 orientation polishes two to four times faster than the 110 orientation. FIG. 22 shows an FIB image for a tungsten layer, the image having a scale of 10 micrometers. In this image, lighter areas (114 orientation) can easily be seen to dominate over the darker areas (110 orientation). It is known that one of the primary causes of the variation in CMP removal rate and the failure of some of the wafer lots with respect to endpoint detection due ratio of orientation components is the drastically differential oxidation reaction rates of orientation faces, such as the 114 and 110 orientations of the tungsten crystal shown in FIG. 22. The novel FIB technique described above provides the ability to quantify the area fraction of the respective orientation components and from the quantification, determine the required CMP removal rate directly. The FIB technique also allows monitoring the wafers at deposition to determine the stability of the process, for example if crystals are being deposited in a desired orientation.

Accordingly, ion channeling contrast images can be used to determine single fiber textural strength and dual fiber texture strength and area fraction. Because ion channeling is responsive to depth in a crystalline structure, area fraction and crystallographic deviations versus depth in a metallic film, for example, may be determined. For example, by determining the crystallographic makeup for a particular area of the sample at varying depths, a three dimensional reconstruction of the sample surface crystallography may be made. Using information regarding crystal orientation data, reconstruction of CMP removal rate curves can be accomplished for more efficient CMP of an inline imaged sample.

C. Dual FIB

Figure 23:
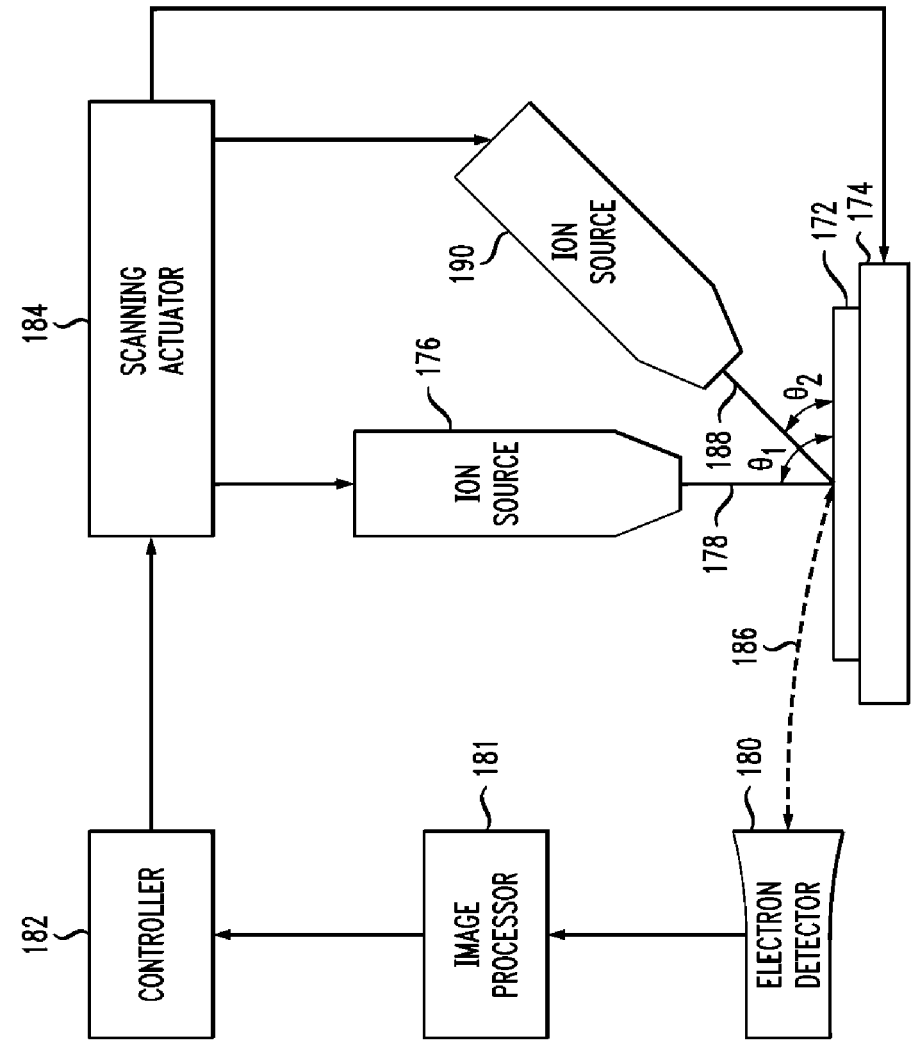
FIG. 23 shows an ion beam embodiment of an inline metrology element for scanning a crystalline sample to detect on axis and off axis channeling response.

Referring now to FIG. 23, an ion beam embodiment of an inline metrology element 170 for scanning a crystalline sample 172 for on axis and off axis channeling response, will now be described. The metrology element 170 includes a sample holder 174 for holding the sample 172 at a glancing angle θ1, such as an on axis channeling angle, to an ion beam 178, and at a second glancing angle θ2, such as an off axis channeling angle, to an ion beam 188. In an aspect of the invention, the glancing angle θ1 is 90 degrees from the face of the crystalline sample 172, while the glancing angle θ2 can be varied from 0 to 90 degrees. The ion beams 178, 188 are generated by respective ion sources 176, 190, such as FIB sources. A scanning actuator 184 is provided for controlling relative movement between the ion beams 178, 188 and the crystalline sample 172 on the sample holder 174. The scanning actuator 184 is controllable for directing the ion beams 178, 188 at selected areas of the crystalline sample 172. In other words, the scanning actuator 184 may control movement of the ion sources 176, 190 to move the ion beams 178, 188 relative to the sample 172 on the sample holder 174, or the scanning actuator 184 may control movement of the sample holder 174 relative to the ion beams 178, 188, or both. In an aspect of the invention, the ion beams 178, 188 are positioned to aim at same spot on the sample 172 to provide an on axis and off axis channeling response for the selected spot. An electron detector 180 is provided to detect electrons 186 emitted from the surface of the sample 172 as the ion sources 176, 190 scan the respective ion beams 178, 188 across the sample 172. In an aspect of the invention, the electron is mounted perpendicular to the ion beam 178 near the edge of sample as shown in FIG. 23.

An image processor 181 may be provided to process contrast images received by the electron detector 180, e.g., by intensifying and/or amplifying the images. Once an image has been processed for a specific area, a controller 182 provides a control signal to the scanning actuator 184 to move the ion beams 178, 188, or the sample holder 174, to another desired area of the sample 172. In an aspect of the invention, the ion sources 176, 190 may be moved in concert to remain aimed at a single desired spot on the sample 172, or may be moved independently.

As described above with respect to a single FIB embodiment mounted normal to the sample 172, the intensity of the secondary electron emission in polycrystalline samples can captured by an electron detector 180 as the ion beams 178, 188 are scanned across the sample 172. Accordingly, an ion beam normal to the surface, such as ion beam 178, and on axis with respect to the channeling directions of the sample 172 can be used to image grain location. In addition, an ion beam not normal to the wafer surface, such as ion beam 188, and off axis with respect to the channeling directions of the sample 172, can be used to image grain size. Therefore, both grain size and grain location of a wafer can be imaged using, for example, a pair of FIB's, to provide inline analysis of a wafer process that can be used to control both a metal deposition process and a CMP process.

An additional feature of having two ion beams is that one ion beam 178, positioned parallel to a normal to the sample surface, may be used as one reference. The other ion beam, 188, which is not aligned with the normal to the sample surface, can be used to determine a secondary contrast intensity. Then, by rotating the sample about ion beam 178, the ion beam 188 can be used to collect a series of contrast intensity images which collectively can be used, along with crystal symmetry data, to reconstruct the discrete crystallographic makeup of the sample surface. This method my enable the determination of the sample crystallography without the need for a channeling reference, such as a crystal reference, to set the contrast intensities.

D. Combination SEM/FIB

Figure 24:
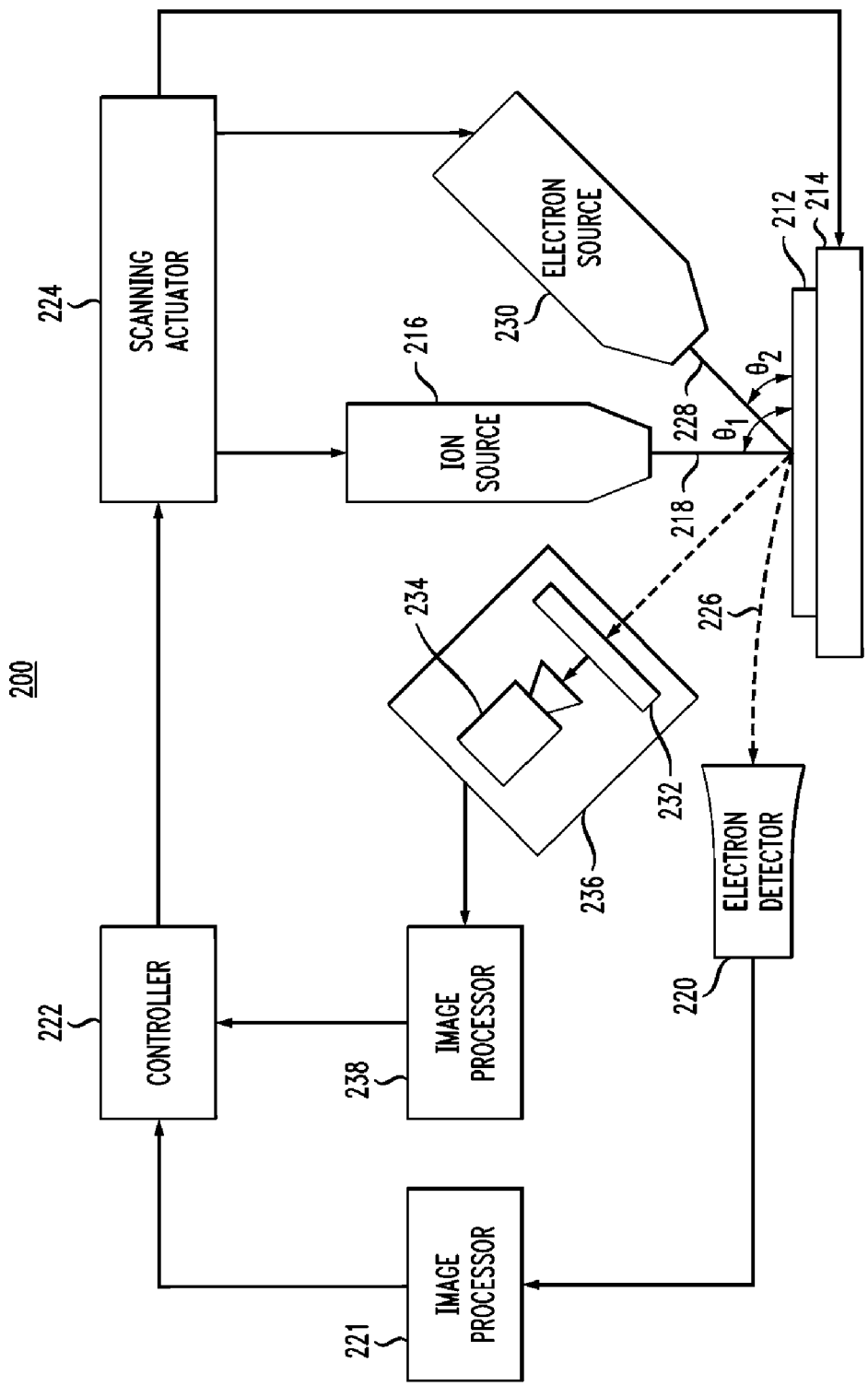
FIG. 24 shows an inline metrology element combining and electron source and ion source for scanning a crystalline sample.

Referring now to FIG. 24, an inline metrology element 200 combining and electron source 230 and ion source 216 for scanning a crystalline sample 212, will now be described. The metrology element 210 includes a sample holder 214 for holding the sample 212 at a glancing angle θ1 to an ion beam 218 and glancing angle θ2 to an electron source 230. In an aspect of the invention, the glancing angle θ1 is 90 degrees from the face of the crystalline sample 212. In another embodiment, the glancing angle θ1 may be an angle between 0 and 90 degrees. The ion beam 218 is generated by an ion source 216, such as a focused ion beam (FIB). A scanning actuator 224 is provided for controlling relative movement between the ion beam 218 and the crystalline sample 212 on the sample holder 214. The scanning actuator 224 is controllable for directing the ion beam 218 at selected areas of the crystalline sample 212. In other words, the scanning actuator 224 may control movement of the ion source 216 to move the ion beam 218 relative to the sample 212 on the sample holder 214, or the scanning actuator may control movement of the sample holder relative to the electron beam, or both. An electron detector 220 is provided to detect electrons 226 emitted from the surface of the sample 212 as the ion source 216 scans the ion beam 218 across the sample 212. In an aspect of the invention, the electron detector 220 is mounted perpendicular to the ion beam 18 near the edge of sample as shown in FIG. 24.

The electron beam 228 is generated by an electron source 230. A scanning actuator 224 is provided for controlling relative movement between the electron beam 228 and the crystalline sample 212 on the sample holder 14. In an aspect of the invention, glancing angle θ2 is 20 degrees. The scanning actuator 224 is controllable for directing the electron beam 228 at the sample 212, for example, in a series of spaced apart points of the crystalline sample 212. In other words, the scanning actuator 224 may control movement of the electron source 216 to move the electron beam 218 relative to the sample 212 on the sample holder 214, or the scanning actuator may control movement of the sample holder relative to the electron beam, or both.

An image processor 236 is provided to process images formed on a phosphor screen 232, e.g., by intensifying and/or amplifying the images. The image processor 236 may comprise a low light or charged coupled device (CCD) camera 234 to capture the images. The phosphor screen 232 is mounted adjacent the sample holder 214 so that it is parallel to the incident electron beam 218. Diffracted electrons from the sample 212 form images on the phosphor screen 232 as described with respect to FIG. 1. These images are known as Kikuchi diffraction patterns and include Kikuchi bands, which can be used to determine the crystallographic grain orientation at a point within a scan area of the sample 212. In addition, another image processor 221 may be provided to process contrast images received by the electron detector 220, e.g., by intensifying and/or amplifying the images. Once an image has been processed for a specific area, a controller 222 provides a control signal to the scanning actuator 224 to move the ion beams 218, or the sample holder 214, to another desired area of the sample 212. In an aspect of the invention, the ion source 216 and electron source 230 may be moved in concert to remain aimed at a desired single spot on the sample 212, or moved independently.

Accordingly, by using both an electron source 230 and an ion source 216 in a dual configuration, efficient crystallographic inline analysis can be performed. For example, the ion beam can be used for grain identification and an electron beam can be used in point diffraction mode to determine orientation in a crystalline. In an aspect of the invention, the ion beam can be used to grossly determine grain boundary locations, while the electron beam 228 can be used in analytical mode if finer crystallographic analysis, such as by using diffraction patterns, is required. For example, a sample of aluminum with a preferred orientation of (111) could be analyzed with an off-axis channeling measurement (that is, with an angle of, for example, 5 degrees between the incident ion beam and the surface normal or θ2 equal to 90 degrees). In an off axis configuration, the grains would yield different contrast intensities. From an ion channeling contrast image, the grain boundaries may be identified and the individual grains determined. Then, the ion beam can be disengaged, and the electron beam may take a diffraction measurement from the center of each of the identified grains. Accordingly, both morphological information from the channeling contrast image, and discrete crystallographic information from the electron beam measurement, can be provided. Combining the two data sources can enable a full crystallographic characterization of the sample surface.

In another aspect of the invention, the off-axis measurement technique described above can be used to center, or provide a reference for, an on-axis, (θ1 equal to 90 degrees) method of ion channeling contrast determination. Therefore, the two beam method may be used to set the parameters and provide a reference for the single ion beam measurement. In practice, the first sample can be solved discretely by off-axis grain identification, followed by on-axis discrete solving of the crystallographic information. The sample may then be measured using the on-axis method with the off-axis method providing reference. Once a reference is determined and contrast levels set for the different crystallographic directions, the rest of the sample set may only require the use of single ion beam for crystallography. This allows increasing throughput of the sample sets while still allowing for a full crystallographic characterization of the sample surfaces.

In another aspect of this invention, a full determination of the morphology and crystallography can be performed at each cross sectional plane through the sample followed by a three dimensional crystallographic reconstruction done.

III. FIB Crystal Standard

In ion beam imaging techniques, setting up a contrast scale using trial and error techniques can be problematic. In particular, centering a scale of contrast for a secondary electron emission image for determining crystallographic orientations in a sample can be difficult to achieve. The inventors of the present invention have innovatively realized that by creating a dual orientation fiber texture metrology standard for providing a reference to set a contrast scale in ion imaging. For example, a bicrystal with grain boundaries specific to the rotation angle boundaries between the two orientations can be used as a standard.

Figure 25:
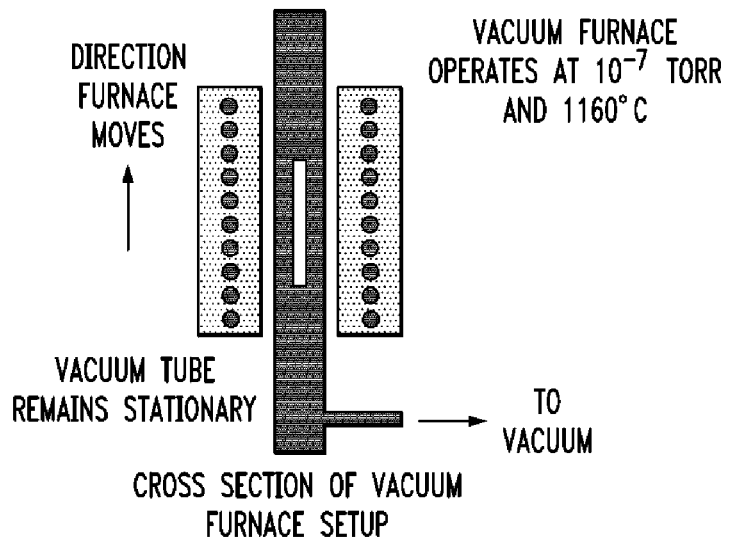
FIG. 25 depicts a vertical Bridgman vacuum furnace system for growing a bicrystal standard.
Figure 26:
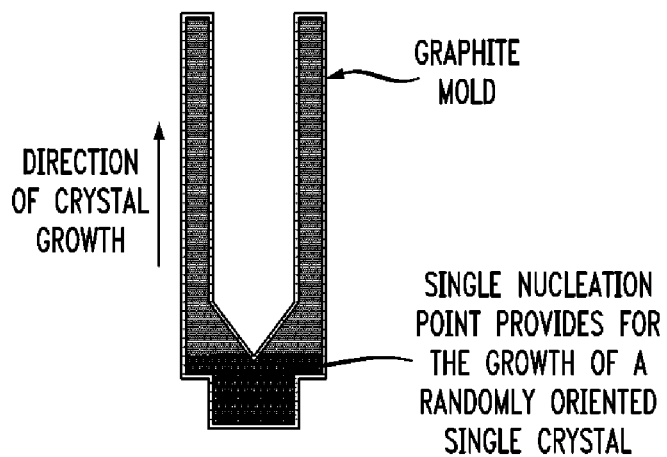
FIG. 26 depicts graphite mold having a single nucleation site for growing a pure single crystal of random orientation.
Figure 27:
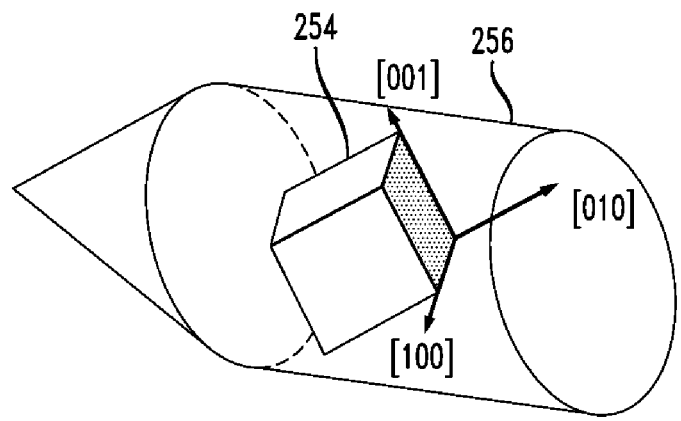
FIG. 27 shows a seed crystal that can be extracted at a misorientation angle from a pure single crystal.
Figure 28:
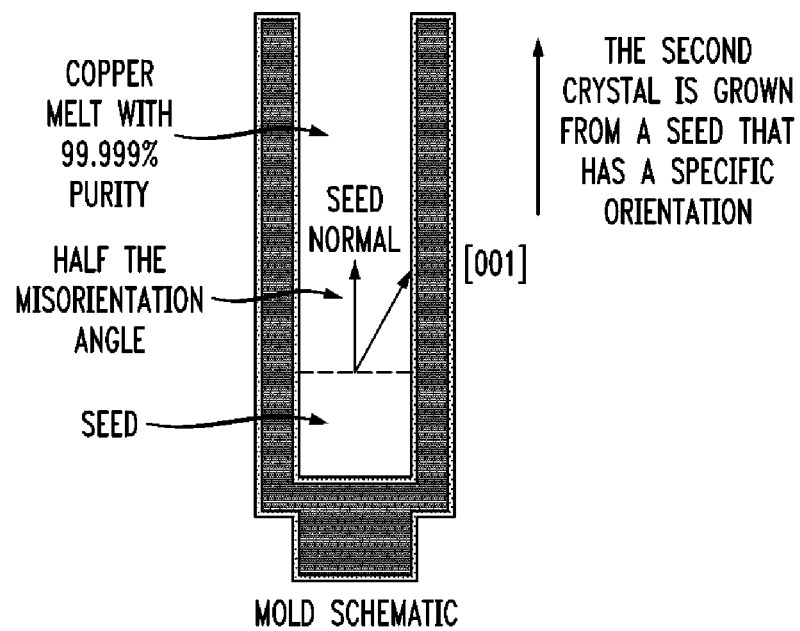
FIG. 28 depicts a graphite mold to form a seed grown crystal from a pure single seed crystal.
Figure 29:
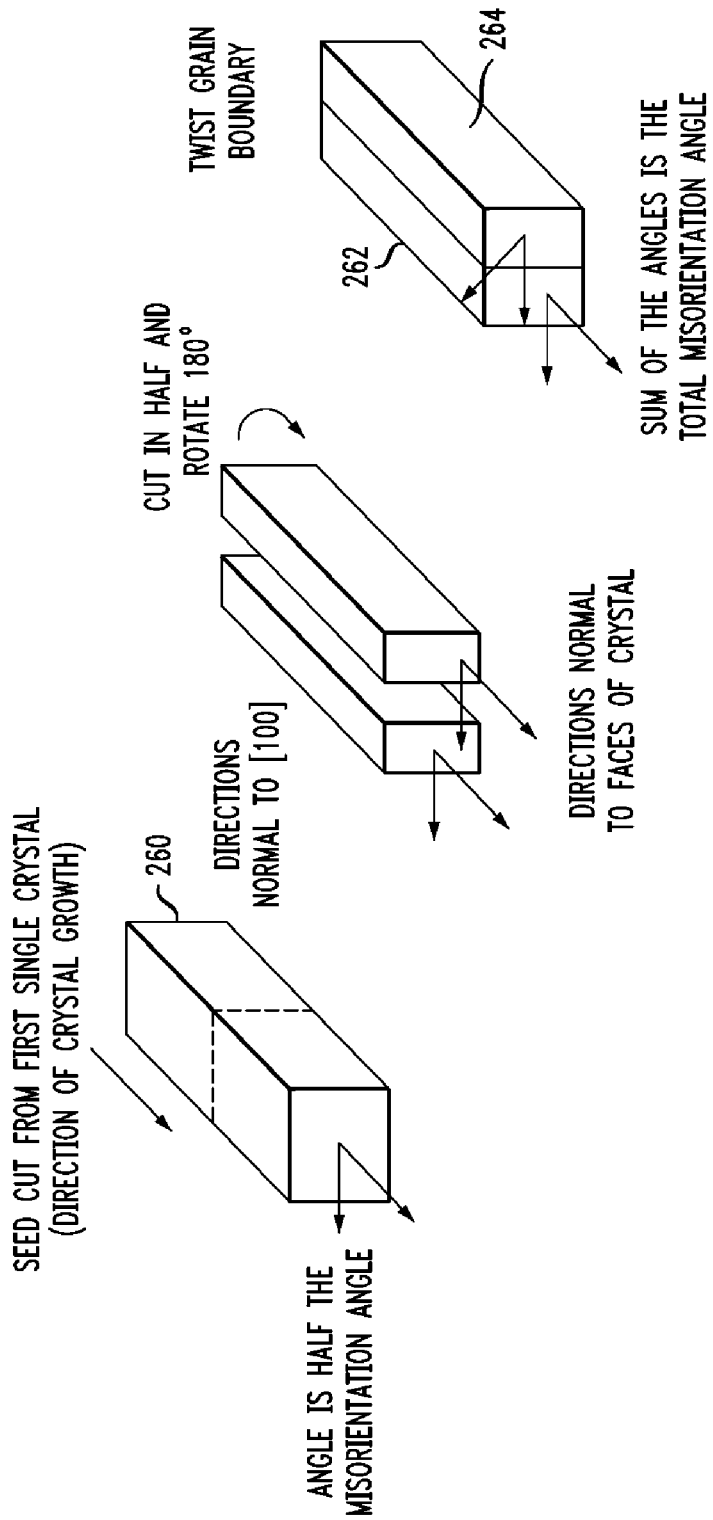
FIG. 29 depicts the stages of cutting a seed grown crystal into two bicrystal seeds halves.
Figure 30:
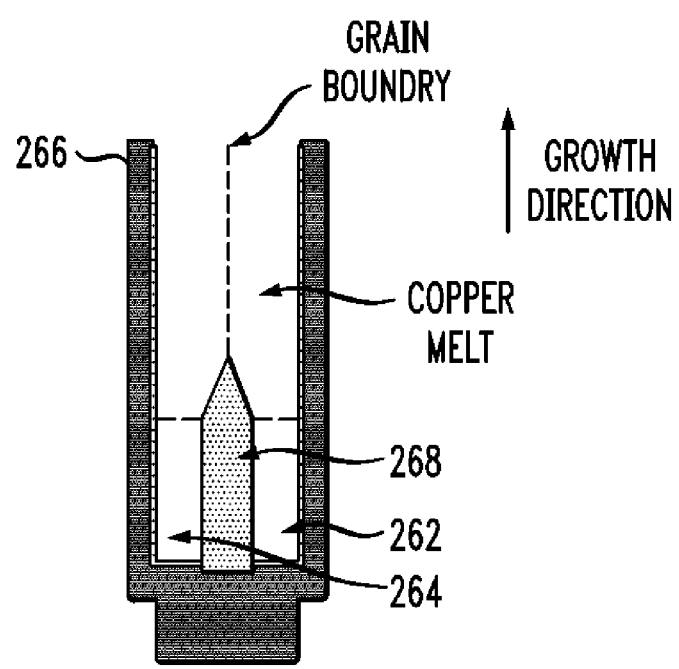
FIG. 30 depicts a graphite bicrystal mold for forming a bicrystal from bicrystal seeds halves.
Figure 31:
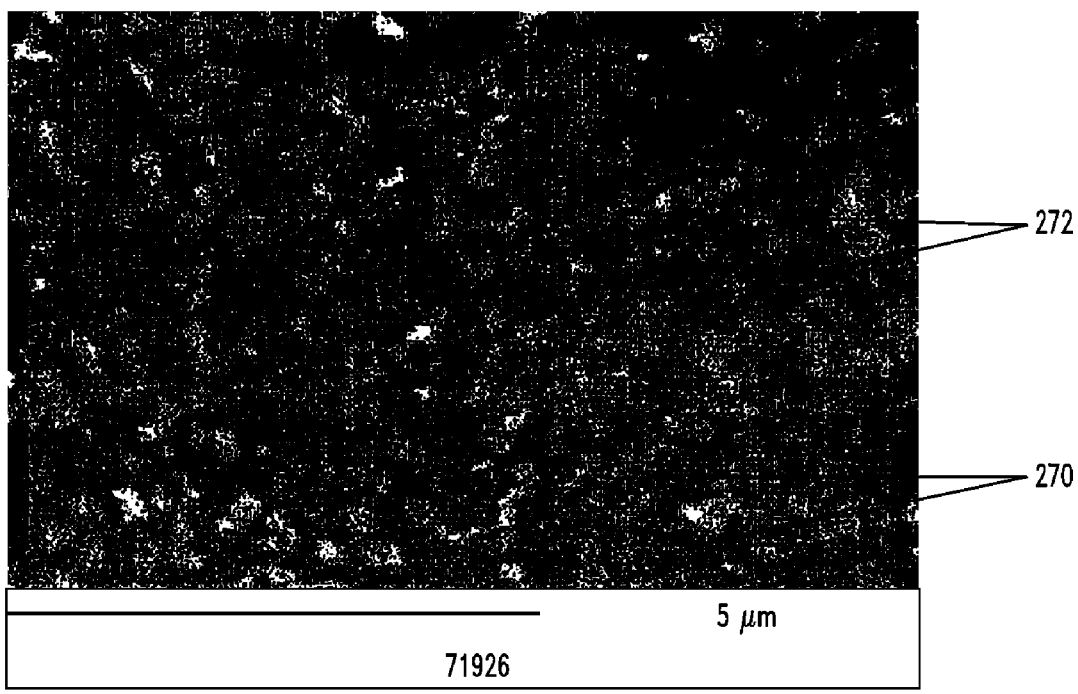
FIG. 31 is a tungsten ion beam channeling contrast image.

FIG. 25 depicts a vertical Bridgman vacuum furnace system 250 for growing a bicrystal according to the invention. FIG. 26 depicts a graphite mold 252 having a single nucleation site for growing a pure single crystal of random orientation. FIG. 27 shows a seed crystal 254 that can be extracted at a misorientation angle from a pure single crystal 256. As depicted in FIG. 27, the seed crystal 254 can be cut from the first crystal 256 of random orientation grown in the mold 252, so that the orientation of the seed crystal 256 incorporates half a misorientation angle rotated about the 001 axis. The seed crystal 254 can then be ground and polished at a reference face so that the normal with respect to the 001 axis is half the misorientation angle. FIG. 28 depicts a graphite mold 258 to form a seed grown crystal from a pure single seed crystal. The seed crystal 256 is placed in another graphite mold 258 and a seed grown crystal, having a specific orientation, is grown. FIG. 30 depicts the stages of cutting a seed grown crystal 260 into two bicrystal seeds halves 262, 264. As shown in FIG. 29, the seed grown crystal 260 is cut into two bicrystal seeds halves 262, 264 in a direction parallel to the growth direction, one half 264 is rotated 180 degrees and oriented with respect the other half 262 so that a symmetrical twist grain boundary separates the two crystals halves 262, 264.

FIG. 30 depicts a graphite bicrystal mold 266 for forming a bicrystal from bicrystal seeds halves 262, 264. As shown in FIG. 30, the graphite bicrystal mold 266 accommodates a graphite sleeve 268 that keeps bicrystal seeds halves 262, 264 separated during the growing process and enforces the correct orientation for each bicrystal seeds halves 262, 264. The resulting bicrystal exhibits a specific grain boundary.

The bicrystal misorientation can be characterized by using BKD methods as described previously. The patterns can be indexed about the orientations of each crystal of the bicrystal determined. The misorientation, if then described as a rotation of one crystals about a common axis, that brings into coincidence with the second crystal axis/angle. The calculation for misorientation can be written in terms of matrices:

$$[X]1 = [R][X]2 \quad [6]$$

In the above equation, [X]1 and [X]2 are the normalized orientation vectors for component crystals 1 and 2, (for example, crystals 262 and 264) respectively, of the bicrystal and [R] is the rotation matrix. From the rotation matrix, the axis/angle pair can be calculated as follows, wherein angle of rotation:

$$q = \cos^{-1}[0.5(R11 + R22 + R33 - 1)]. \quad [7]$$

The rotation axis (hkl) is:

$$h = (R32 - R23)/(2 \sin q);$$

$$k = (R13 - R31)/(2 \sin q); \text{and}$$

$$i = (R21 - R12)/(2 \sin q). \quad [9]$$

Once the bicrystal is grown, the bicrystal can be used as a standard to correlate the contrast level with the grains imaged by channeling contrast. For example, as shown, in the, appropriated scaled contrast levels reveal light areas 272 characteristic of 114 grain orientations and dark areas 270 characteristic of 110 grain orientations.

IV. Methods for Inline Metrology

As described above with respect the use of an SEM, several novel variable scan methods can be employed to monitor a deposition process, including statistical crystallographic orientation, statistical grain size, and electron line differential to determine boundaries in crystalline substrates. In addition, a novel ion channel technique, as described previously with respect to the use of an FIB, can be used to determine single fiber texture strength, dual fiber texture strength, area fractions, area fraction v. depth through a film, reconstruction of CMP removal rate curves from orientation data, and crystallographic changes versus depth profile. In the previously described dual ion beam/electron beam device, a novel method of channeling contrast of grain locations and point electron diffraction for orientation, and ion channeling for fast inline methodology of problem identification and a slower analytical mode for detailed analysis was described. In addition, information derived from such metrology can be used to provide control parameters to other processes such as a CMP process and a metal deposition process. Other methods for process monitoring and control of a semiconductor fabrication process will now be described.

A. Roughness Correlated Reflectivity

It is known that polycrystalline materials having preferred crystal plane orientations grow at different rates for different orientations. As polycrystalline material begins to nucleate and grow on a sample surface, a characteristic of the material known as the Gibbs surface energy defines the rate at which a crystalline surface will grow. The Gibbs surface energy is different for different orientations as the orientation of the surface defines the angle of the orbital for binding. For a surface that has a tendency to nucleate and grow in a single direction, such as aluminum, the surface energy with respect to a specific planar location should be relatively equivalent resulting in a fairly uniform surface growth rate. Fro poly crystalline materials that nucleate out and grow in different orientations, such as tungsten, different surface energies resulting in different growth rates for each of the different polycrystalline orientations. This differential growth rate effectively creates surface roughness that can be monitored through a variety of monitoring techniques such as reflectivity, SEM analysis, and atomic force microscopy.

Figure 32B:
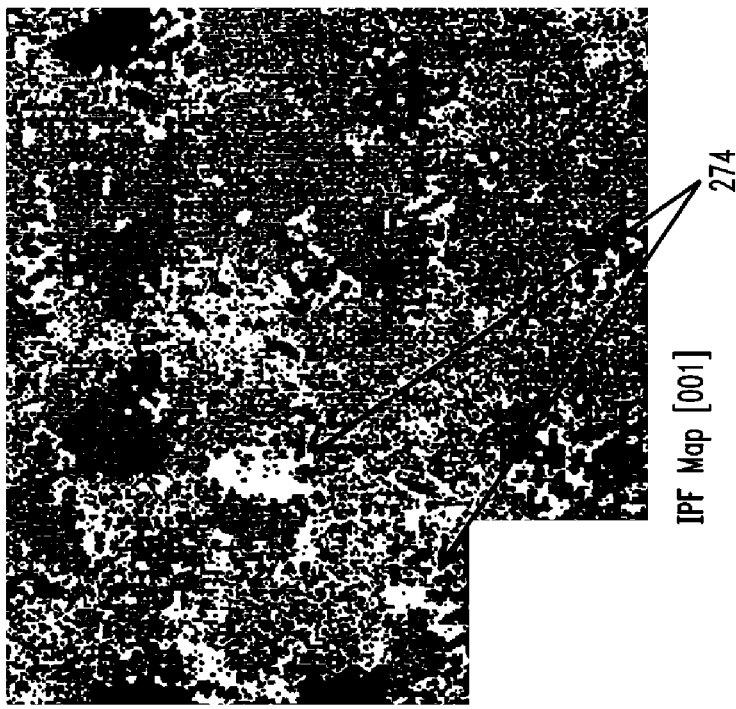
FIG. 32B is an inverse pole map of a relatively smooth tungsten sample imaged using electron beam backscatter.
Figure 32A:
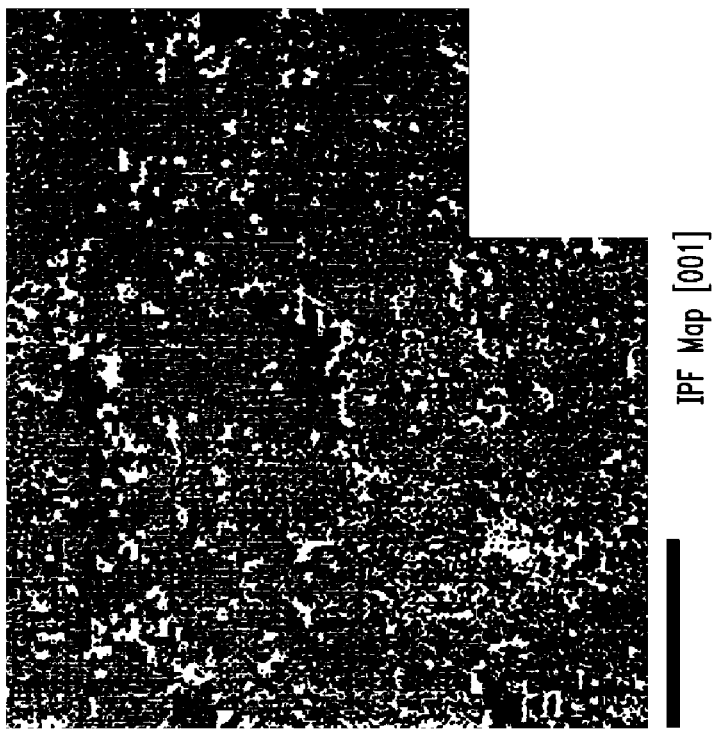
FIG. 32A is an inverse pole map of a relatively rough tungsten sample imaged using electron beam backscatter.

FIG. 33A is an inverse pole map of a relatively rough tungsten sample imaged using electron beam backscatter. FIG. 33B is an inverse pole map of a relatively smooth tungsten sample imaged using electron beam backscatter. As shown in FIG. 32B, a decreased roughness can be correlated to an increased fraction 274 of 110 fiber texture of tungsten.

FIG. 33A is a reflectivity image of a relatively rough tungsten sample having an inset area fraction legend. FIG. 34B is reflectivity image of a relatively smooth tungsten sample having an inset area fraction legend. As shown by visual comparison of the reflectivity images and corresponding area fraction legend, in increase of the area fraction 114 textured orientation (from 0.02 in FIG. 33A to 0.14 in FIG. 33B), decreases the reflectivity that is caused by an increase in the roughness of the film.

B. Uniform Grain Removal Rate Via Differential Dwell Time

It is known that an FIB tool utilizing a focused beam of ions (typically gallium) can remove material from a surface due to the collision cascade of the incident ion beam. Due to channeling effects in polycrystalline structures, certain orientations with respect to the incident ion beam can mill faster or slower then other orientations, thereby causing a surface roughness or non-uniform removal rate during the milling operation. Ion beam removal of a material is one way to either prepare samples or remove material. Accordingly, an FIB can be used for semiconductor defect review, transmission electron beam and scanning transmission electron beam sample preparation and potential for localized metrology.

Previous attempts to solve the problem of non-uniformity of removal rate between grain structures such as channels has been to rotate the sample with respect to the incident beam angle. However, it is difficult to rotate a sample/wafer while maintaining the focus on the surface to control the milling. This technique has been more generally used for gross ion milling whereby the area of removal must be smooth and the orientation is not known or not known to vary with respect to a localized area.

The inventors have innovatively realized that by characterizing differential removal rate with respect to orientation and channeling contrast, the dwell time can be adjusted to compensate for the non-uniform removal rate. Accordingly, polycrystalline materials whereby there is a known or unknown orientation can be milled at a uniform rate.

In recent years, focused ion beam (FIB) instruments have become extremely useful in the microelectronics industry. One of the critical applications of FIB instruments is as a specimen preparation tool for subsequent analysis in scanning electron microscopy (SEM), transmission electron microscopy (TEM), scanning transmission electron microscopy (STEM), secondary ion mass spectrometry (SIMS), and scanning auger microscopy (SAM). Because of the ubiquitous use of Si-based integrated circuits (IC's) and the push toward using Cu in IC metallizations, interest has been directed toward the FIB milling properties of Si and Cu. It is well known that Si exhibits exceptional FIB milling properties, while milling of Cu has been problematic.

An FIB instrument utilizes a finely focused ion beam from, for example, a Ga liquid metal ion source (LMIS) to perform imaging and milling operations. The interaction of the finely focused ion beam with the target material will produce the ejection of secondary electrons, secondary ions, and secondary neutrals. The ions and neutrals can be ejected as individual atoms, molecules, or clusters. The imaging capability of the FIB allows the use of either the secondary electrons or the secondary ions for image formation. Milling operations are achieved through site specific sputtering (as described previously with respect to an FIB inline metrology element) of the target material as described previously with respect to an FIB inline metrology element.

Another particularly interesting capability of the FIB is that it produces ion channeling contrast in the secondary electron images for polycrystalline samples. Ion channeling contrast occurs because the secondary electron yield varies as a function of crystallographic orientation within the sample. Channeling can occur when a crystallographic axis of a particular grain is aligned with the incident ion beam. As a result, that grain will appear darker due in an electron detector image due to a decrease in the number of secondary electrons that are produced.

It has been well established that the sputtering yield is a function of crystallographic orientation. As the ion beam becomes incident in a channeling direction, the sputtering yield will decrease. The main reason for the decrease in the sputtering yield is that the channeled ions undergo mostly electronic energy losses as opposed to nuclear energy losses and are able to penetrate deeper into the crystal lattice. The deeper penetration and the lower probability of nuclear collisions near the surface extremely limits the probability that the ion will cause a collision cascade that will contribute to the sputtering of surface atoms.

Using a Lindhard-Onderdelinden approach for monocrystalline sputtering, the channeling directions and critical angles are calculated for 30 keV Ga+ into Cu using the following seven equations. The channeled sputtering yield Yuvw is related to the amorphous sputtering yield Yamorph with the non-channeled fraction χuvw and a fitting parameter ηhkl as shown in Equation 1.

$$Y_{uvw} = \eta_{hkl} \chi_{uvw} Y_{amorph} \tag{1}$$

The amorphous sputtering yield Yamorph is dependent on the angle of incidence θ and the energy of the incident ion E. The non-channeled fraction χuvw is just the statistical fraction of the beam that contributes to sputtering in the axial channeling direction and is dependent on the critical channeling angle Ψc and the incident ion energy E. The fitting parameter ηhkl will be assumed as unity in order to analyze just the channeling effects. According to the Lindhard-Onderdelinden approach, the non-channeling fraction at normal incidence χouvw can be calculated using the Thomas-Fermi potential for the ion-atom interaction as shown in Equation 2.

$$\chi^o_{uvw} = \pi N r_{uvw}^{3/2} \left[ 3A^2 Z_1 Z_2 \left( \frac{e^2}{4\pi\varepsilon_o} \right) \middle/ E \right]^{1/2} \tag{2}$$

The distance between atom positions along the index direction [uvw] is tuvw. The elemental charge e is 1.60×10-19 C and permittivity constant εo is 8.85×10-12 C2/N*m2. The non-channeled fraction depends on both the atomic density N and the atomic number Z2 of the target material, the atomic number Z1 and energy E of the incident ion, and the Thomas-Fermi screening length A shown in Equation 3. (Note again that this model neglects the effects of planar channeling.)

$$A = \frac{\left( \frac{9\pi^2}{128} \right)^{1/3} a_o}{(Z_1^{2/3} + Z_2^{2/3})^{1/2}} \tag{3}$$

The Thomas-Fermi screening length A depends on the atomic number of both the incident ion and the target material Z1 and Z2 and the Bohr radius ao.

$$a_o = \frac{\eta^2}{m_e \frac{e^2}{4\pi\varepsilon_o}} = 0.529177 \text{Å} \quad (4)$$

Plank's constant divided by 2πη is 1.05×10-34 J*s and the mass of the electron me is 9.11×10-31 kg. With the establishment of the non-channeled fraction at normal incidence χouvw, the channeling directions can be calculated for a given energetic incident ion and a target material. Next, the angular width of the channeling directions, called the critical angle ψc, can be calculated.

$$\psi_c = \left[\frac{3A^2 Z_1 Z_2 \left(\frac{e^2}{4\pi\varepsilon_o}\right)}{Et_{uvw}^3}\right]^{1/4} \quad (5)$$

$$E < E_1 = \frac{2Z_1 Z_2 \left(\frac{e^2}{4\pi\varepsilon_o}\right) t_{uvw}}{A^2} \quad (6)$$

Equation 5 is valid as long as the energy of the incident ion is less than E1, which is the upper limit for Lindhard's low energy approximation according to Equation 6. The calculated upper limit for the case of 30 keV Ga into Cu is ~5.8 MeV. As the ion beam deviates from the direct channeling direction, the non-channeled fraction will increase toward unity as channeling becomes less statistically possible. The polar angle resolved non-channeled fraction is then denoted as χuvw as shown in Equation 7.

$$\chi_{uvw} = \frac{\chi_{uvw}^o}{1 - (1 - \chi_{uvw}^o)\left(\frac{\psi}{f\psi_c}\right)^2} \quad (7)$$

The polar angle from normal incidence along a channeling direction [uvw] is ψ. The fitting parameter f is included in order to accurately fit the model to experimental data. When the ion channeling contrast across the boundary is not uniform, the result is differential sputtering as well as trench wall sloping from re-deposition on half of the specimen. Since the TEM specimen must be a uniform thickness, a modified milling technique must be employed in order to achieve a quality TEM Lift-Out specimen. Using the ion channeling contrast as a guide, the sample can be tilted a few degrees until the ion channeling contrast across the boundary is uniform. The differential sputtering is eliminated and the effects of re-deposition have been reduced in order to achieve the desired uniform thickness of the specimen. Therefore:

$$Y = 4\frac{C}{X} - 3Y_{amorph}$$

C = contrast level

X = scaling factor where X is defined as the value at which $$X = \frac{C_0}{Y_{uvw}(\theta = 0)}$$

$Y_{amorph}$=amorphous sputtering yield at normal incidence

Figure 34:
FIG. 34 shows an ion channeling contrast image of polycrystalline recrystallized copper.

Accordingly, because sputtering yield can be tied to ion channeling contrast, a mechanism for compensation can be developed whereby the depth of material removed is a function of the sputtering yield and the dwell time at a particular location For example, within the sample different grain structures can readily be seen. The twin component of the copper grains is also well visualized. The image in FIG. 34 is created by monitoring the secondary electron output of a primary incident ion beam. Accordingly, the image in FIG. 34 is essentially an ion channeling contrast map of the sample surface.

Figure 35:
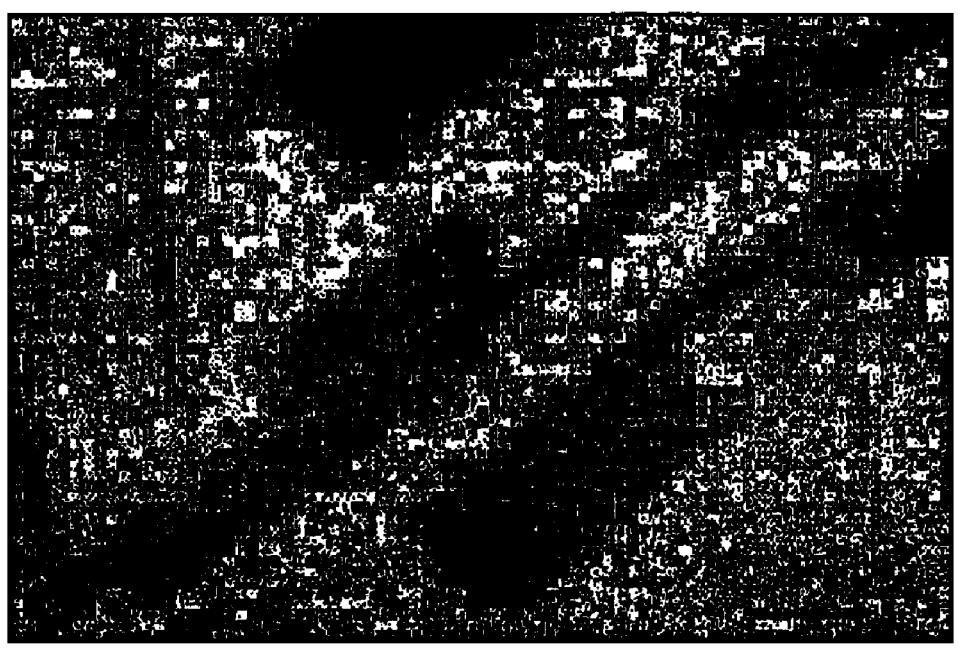
FIG. 35 shows an enlarged view of a selected region of the ion channeling contrast image of FIG. 34.

The incident ion beam can be instructed to dwell (the length of time the primary ion beam spends at any particular location) at each point along a scan. A differential dwell time can be used that is calculated through a scaling function of the ion channeling contrast. For example, for the selected region of copper shown in the image of FIG. 35 a singular grain can be seen and the sigma three FCC annealing twins can be seen as the regions of a darker contrast. For the areas that are darker, the ion beam can be directed to dwell a longer time since the contrast-sputtering yield equations dictate that for darker ion channeling contrasts there is less sputtering yield. For example, FIG. 37A shows an image of a copper bicrystal whereby the difference in contrast levels between the right side 276 of the crystal and the left side 278 of the crystal is a grain boundary 280. When the channeling contrast, a dramatic difference in the depth of the cuts is evident.

Figure 36A:
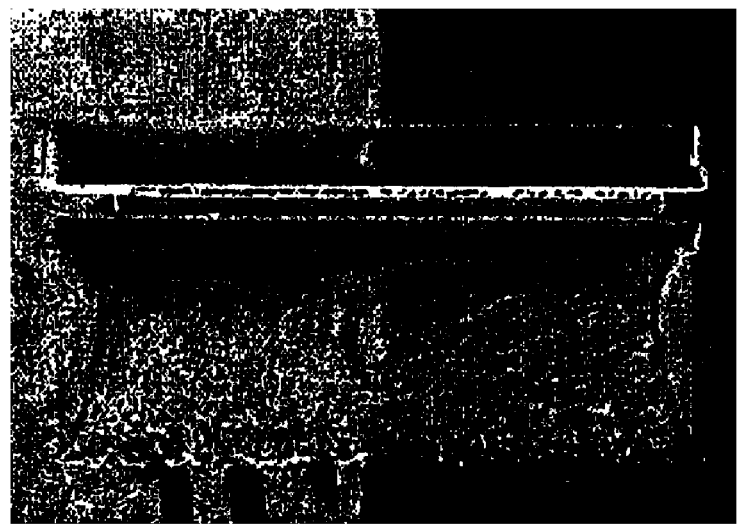
FIG. 36A, shows an ion channeling image of a copper bicrystal.
Figure 36B:
FIG. 36B shows an ion channeling image of a copper bicrystal.

When the contrasts are then equalized as in the image of FIG. 36B, before the milling procedure, an even removal rate across the grain boundary despite the different sides of the boundary have appreciably different orientations. Accordingly, by using ion channeling contrast, differential dwell times can be programmed for different area to maintain a constant sputtering yield over the polycrystalline material.

C. CMP Processing

CMP processing may be controlled using the embodiments described herein. The disclosed methods may be used to maintain an equal plane of material removal though a sample of differing intensity contrasts or removal rates. Once it is determined that the material may be removed in a planar manner, with an effective method of determining the crystallography at each plane, a three dimensional reconstruction of the crystallographic makeup of a sample surface may be obtained. The method may also include determining when to cease removal of the material based on the orientations of crystals of the removal surface.

While the preferred embodiments of the present invention have been shown and described herein, it will be obvious that such embodiments are provided by way of example only. Accordingly, it is intended that the invention be limited only by the spirit and scope of the appended claims.

What is claimed is:

1. A system for crystallography comprising:
   a sample holder for holding a crystalline sample for characterization of a sample area;
   an electron source for generating an electron beam;

a scanning actuator for controlling the relative movement between the electron beam and the crystalline sample, the scanning actuator being controllable for directing the electron beam at a series of spaced apart points within the sample area;

a first processing system for generating crystallographic data based upon electron diffraction from the crystalline sample;

a second processing system configured for determining whether sufficient data have been acquired to characterize the sample area; and a controller for controlling the scanning actuator to space the points apart such that acquired data is representative of a different grains within the crystalline sample.

2. The system of claim 1, further comprising a third processing system for determining grain sizes in the sample area by counting grain boundaries intersecting concentric circles of spaced apart points.

3. The system of claim 1, further comprising a third processing system for determining grain sizes in the sample area by counting grain boundaries along a series of lines of spaced apart points.

4. The system of claim 1, further comprising a feed-forward loop for providing control parameters, based upon the crystallographic data, to a chemical-mechanical polishing station.

5. The system of claim 1, further comprising a feedback loop for providing control parameters to a deposition station based upon the crystallographic data.

6. The system of claim 1, wherein the electron beam is positioned to intercept the sample at an angle of approximately 20 degrees.

7. The system of claim 1, further comprising a crystalline standard for providing a reference to the processing system.

8. A system for inline crystallographic metrology comprising:

a sample holder for holding a crystalline sample;

a first ion source for generating a first ion beam;

a scanning actuator for controlling the relative movement between the first ion beam and the crystalline sample, the scanning actuator being controllable for directing the first ion beam at desired areas of the crystalline sample;

an electron detector for detecting secondary electrons emitted from the crystalline sample;

a first processing system for creating a contrast intensity image based upon secondary electron emissions from the crystalline sample;

a second processing system programmed to provide crystallographic information based on the contrast image intensity data; and a controller for controlling the scanning actuator for scanning the first ion beam.

9. The system of claim 8, further comprising a feed-forward loop for providing control parameters to a chemical-mechanical polishing station based upon acquired data.

10. The system of claim 8, further comprising a feedback loop for providing control parameters to a deposition station based upon acquired data.

11. The system of claim 8, wherein the first ion beam is positioned to intercept the crystalline sample at an angle of approximately 90 degrees.

12. The system of claim 8, further comprising a crystalline standard for providing a reference to the processing system.

13. The system of claim 8, further comprising a second ion source for generating a second ion beam, the second ion source controllable by the scanning actuator.

14. The system of claim 13, wherein the second ion beam is positioned to intercept the crystalline sample at angle of between 0 degrees and 90 degrees.

15. A system for inline crystallographic metrology comprising:

a sample holder for holding a crystalline sample;

a first ion source for generating a first ion beam;

an electron source for generating an electron beam;

a scanning actuator for controlling the relative movement between the first ion beam, the electron beam, and the crystalline sample, the scanning actuator being controllable for directing the first ion beam at desired areas of the crystalline sample and for directing the electron beam at a series of points within the sample area;

an electron detector for detecting secondary electron emissions from the crystalline sample;

a first processing system for creating a contrast intensity image based upon secondary electron emissions from the crystalline sample and generating crystallographic data based upon electron diffraction from the crystalline sample;

a second processing system programmed to provide crystallographic information based on the contrast image intensity data and configured for determining whether sufficient data have been acquired to characterize the sample area; and a controller for controlling the scanning actuator to direct the first ion beam at desired areas such that each ion channeling image is representative of channeling directions within the crystalline sample and to space the points apart such that acquired data is representative of a different grains within the crystalline sample.

16. The system of claim 15, further comprising a feed-forward loop for providing control parameters to a chemical-mechanical polishing station based upon acquired data.

17. The system of claim 15, further comprising a feedback loop for providing control parameters to a deposition station based upon acquired data.

18. The system of claim 16, wherein the electron beam is positioned to intercept the sample at an angle of approximately 20 degrees.

19. The system of claim 16, further comprising a crystalline standard for providing a electron diffraction reference to the processing system.

20. The system of claim 16, further comprising a crystalline standard for providing an ion channeling reference to the processing system.

21. The system of claim 16, wherein the ion beam is positioned to intercept the crystalline sample at an angle of approximately 90 degrees.

22. A method for determining crystallography of bulk crystal sample comprising:

providing a sample holder for holding a crystalline sample for characterization of a sample area;

generating an electron beam;

controlling the relative movement between the electron beam and the crystalline sample to direct the electron beam at a series of spaced apart points within the sample area;

generating crystallographic data based upon electron diffraction from the crystalline sample;

determining whether sufficient data have been acquired to characterize the sample area; and spacing the points apart such that acquired data is representative of a different grain within the crystalline sample.

23. The method of claim 22, further comprising determining grain sizes in the sample area by counting grain boundaries intersecting concentric circles of spaced apart points.

24. The system of claim 22, further comprising determining grain sizes in the sample area by counting grain boundaries along a series of lines of spaced apart points.

25. The system of claim 22, further comprising providing feed-forward control parameters, based upon the crystallographic data, to a chemical-mechanical polishing station.

26. The method of claim 22, further comprising controlling polarity of a chemical-mechanical polishing slurry to modify relative material removal rates from different crystalline planes of a crystalline sample to allow consistent endpoint prediction of the chemical-mechanical polishing process.

27. The method of claim 22, further comprising providing feedback control parameters to a deposition process based upon the acquired data.

28. The method of claim 22, further comprising positioning the electron beam to intercept the sample at an angle of approximately 20 degrees.

29. The method of claim 22, further comprising setting data processing parameters based on a crystallographic standard.

30. A method for determining crystallography of bulk crystal sample comprising:
providing a sample holder for holding a crystalline sample;
generating a first ion beam;
controlling the relative movement between the first ion beam and the crystalline sample, for directing the first ion beam at desired areas of the crystalline sample;
detecting secondary electrons emitted from the crystalline sample;
creating a contrast intensity image based upon secondary electron emissions from the crystalline sample;
providing crystallographic information based on the contrast image intensity data; and
controlling the scanning actuator for scanning the first ion beam.

31. The method of claim 30, further comprising providing control parameters, based upon processed emission data, to a chemical-mechanical polishing process.

32. The method of claim 31, further comprising controlling polarity of a chemical-mechanical polishing slurry to modify relative material removal rates from different crystalline planes of a crystalline sample to allow consistent endpoint prediction of the chemical-mechanical polishing process.

33. The method of claim 30, further comprising providing control parameters, based upon processed emission data, to a deposition process.

34. The method of claim 30, further comprising positioning the first ion beam to intercept the crystalline sample at an angle of approximately 90 degrees.

35. The method of claim 30, further comprising directing the first ion beam at desired areas of the crystalline sample in a desired direction such that processed emission data is representative of channeling directions within the crystalline sample.

36. The method of claim 35, further comprising rotating the sample about an axis of the incident first ion beam to align the first ion beam with a channeling direction of the sample.

37. The method of claim 30, further comprising setting emission data processing parameters based on a crystallographic standard.

38. The method of claim 30, further comprising providing a second ion source for generating a second ion beam.

39. The method of claim 38, further comprising positioning the second ion beam to intercept the crystalline sample at angle of between 0 degrees and 90 degrees.

40. The method of claim 38, further comprising determining a reference contrast setting by:
rotating the crystalline sample about the longitudinal axis of the first ion beam;
collecting a series of contrast intensity images generated by the first and second ion beams; and
comparing the collected contrast intensity images to reconstruct the crystallography of the crystalline sample.

41. The method of claim 30, further comprising using crystallographic information to determine crystallographic parameters of the bulk crystal sample selected from the group consisting of single fiber texture strength, dual fiber texture strength, area fraction, area fraction versus depth through a film, reconstruction of CMP removal rate curves from orientation data, and crystallographic changes versus depth profile.

42. A method for determining crystallography of bulk crystal sample comprising:
providing a sample holder for holding a crystalline sample;
generating a first ion beam;
generating an electron beam;
controlling the relative movement between the first ion beam, the electron beam, and the crystalline sample for directing the first ion beam at desired areas of the crystalline sample and for directing the electron beam at a series of points within the sample area;
detecting secondary electron emissions from the crystalline sample;
creating a contrast intensity image based upon secondary electron emissions from the crystalline sample and generating crystallographic data based upon electron diffraction from the crystalline sample;
providing crystallographic information based on the contrast image intensity data and configured for determining whether sufficient data have been acquired to characterize the sample area; and
controlling the scanning actuator to direct the first ion beam at desired areas such that each ion channeling image is representative of channeling directions within the crystalline sample and spacing the points apart such that acquired data is representative of a different grains within the crystalline sample.

43. The method of claim 42, further comprising spacing the points apart sufficient distances such that diffraction data received from the points emanates from different grains of the crystalline sample.

44. The method of claim 42, further comprising directing the first ion beam at desired areas of the crystalline sample in a desired direction such that emission data is representative of channeling directions within the crystalline sample.

45. The method of claim 44, further comprising rotating the sample about an axis of the incident first ion beam to align the first ion beam with a channeling direction of the sample.

46. The method of claim 42, further comprising providing control parameters, based upon processed emission data and diffraction data, to a chemical-mechanical polishing process.

47. The method of claim 46, further comprising controlling polarity of a chemical-mechanical polishing slurry to modify relative material removal rates from different crystalline planes of a crystalline sample to allow consistent endpoint prediction of the chemical-mechanical polishing process.

48. The method of claim 42, further comprising providing control parameters, based upon processed emission data and diffraction data, to a deposition process.

49. The method of claim 42, further comprising positioning the electron beam to intercept the sample at an angle of approximately 20 degrees.

50. The method of claim 42, further comprising further comprising setting data processing parameters based on a crystallographic standard.

51. The method of claim 42, further comprising positioning the first ion beam to intercept the crystalline sample at an angle of approximately 90 degrees.

52. The method of claim 42, further comprising using crystallographic information to determine crystallographic parameters of the bulk crystal sample selected from the group consisting of single fiber texture strength, dual fiber texture strength, area fraction, area fraction versus depth through a film, reconstruction of CMP removal rate curves from orientation data, and crystallographic changes versus depth profile.

* * * * *